US007476679B2

(12) United States Patent
Carroll et al.

(10) Patent No.: US 7,476,679 B2
(45) Date of Patent: Jan. 13, 2009

(54) OCTAHYDROISOQUINOLINE COMPOUNDS AS OPIOID RECEPTOR MODULATORS

(75) Inventors: Frank Ivy Carroll, Durham, NC (US); Hernan A Navarro, Chapel Hill, NC (US); S. Wayne Mascarella, Hillsborough, NC (US); James B. Thomas, Efland, NC (US)

(73) Assignee: Research Triangle Institute, Research Triangle Park, NC (US)

( * ) Notice: Subject to any disclaimer, the term of this patent is extended or adjusted under 35 U.S.C. 154(b) by 329 days.

(21) Appl. No.: 11/189,068

(22) Filed: Jul. 26, 2005

(65) Prior Publication Data

US 2007/0027182 A1 Feb. 1, 2007

(51) Int. Cl.
C07D 217/02 (2006.01)
A61K 31/47 (2006.01)

(52) U.S. Cl. ...................... 514/307; 546/140
(58) Field of Classification Search ................ None
See application file for complete search history.

(56) References Cited

U.S. PATENT DOCUMENTS

| | | | |
|---|---|---|---|
| 4,029,796 A | 6/1977 | Zimmerman et al. |
| 5,128,118 A | 7/1992 | Carroll et al. |
| 5,141,959 A | 8/1992 | Carroll et al. |
| 5,298,499 A | 3/1994 | Carroll et al. |
| 5,380,848 A | 1/1995 | Kuhar et al. |
| 5,413,779 A | 5/1995 | Kuhar et al. |
| 5,496,953 A | 3/1996 | Kuhar et al. |
| 5,736,123 A | 4/1998 | Carroll |
| 5,831,095 A | 11/1998 | Gonzalez et al. |
| 5,935,953 A | 8/1999 | Kuhar et al. |
| 5,968,949 A | 10/1999 | Dondio et al. |
| 6,123,917 A | 9/2000 | Carroll |
| 6,329,520 B1 | 12/2001 | Carroll et al. |
| 6,358,492 B1 | 3/2002 | Kuhar et al. |
| 6,416,735 B1 | 7/2002 | Carroll et al. |
| 6,479,509 B1 | 11/2002 | Carroll |
| 6,531,481 B2 | 3/2003 | Carroll et al. |
| 6,531,483 B1 | 3/2003 | Kuhar et al. |
| 6,538,010 B1 | 3/2003 | Carroll |
| 6,552,032 B2 | 4/2003 | Carroll et al. |
| 6,559,159 B2 | 5/2003 | Carroll et al. |
| 6,593,348 B2 | 7/2003 | Carroll et al. |
| 6,706,880 B2 | 3/2004 | Carroll et al. |
| 6,900,228 B1 | 5/2005 | Carroll et al. |
| 2002/0132828 A1 | 9/2002 | Carroll et al. |
| 2002/0188003 A1 | 12/2002 | Kuhar et al. |
| 2003/0157415 A1 | 8/2003 | Carroll et al. |
| 2003/0176434 A1 | 9/2003 | Carroll |
| 2003/0203934 A1 | 10/2003 | Kuhar et al. |
| 2004/0146518 A1 | 7/2004 | Carroll et al. |
| 2007/0027182 A1 | 2/2007 | Carroll et al. |

OTHER PUBLICATIONS

U.S. Appl. No. 11/863,587, filed Sep. 28, 2007, Kuhar et al.
U.S. Appl. No. 11/272,492, filed Nov. 14, 2005, Carroll.
U.S. Appl. No. 11/189,068, filed Jul. 26, 2005, Carroll et al.
U.S. Appl. No. 12/105,814, filed Apr. 18, 2008, Carroll et al.
T. Nogrady, Medicinal Chemistry, "A Biochemical Approach", Oxford University Press, New York, 1985, p. 68.
H. Awaya, et al., "Racemic and Optically Active 2,9-Dimethyl-5-(m-hydroxyphenyl)morphans and Pharmacological Comparison with the 9-Demethyl Homologues", J. Med. Chem., 1984, 27, pp. 536-539.
H. Awaya, et al., "Hexahydro-1H-1-pyrindines from Acid Rearrangement of 9-Alkylidene-5-(m-methoxyphenyl)-2-methylmorphans. A New Structural Type of Narcotic Antagonists", J. Med. Chem., 1987, 30, pp. 947-950.
F. Ivy Carroll, et al., Journal of Medicinal Chemistry, vol. 47, No. 2, Jan. 15, 2004, pp. 281-284.
D. Zimmerman, et al., "Structure-Activity Relationship of trans-3,4-Dimethyl-4-(3-hydroxyphenyl)piperidine Antagonists for µ-and κ-Opioid Receptors", Journal of Medicinal Chemistry, vol. 36, No. 20, Oct. 1, 1993, pp. 2833-2841.
M. Statnick, et al., "Na$^+$-dependent High Affinity Binding of [$^3$H]LY515300, a 3,4-Dimethyl-4-(3-hydroxyphenyl)piperidine Opioid Receptor Inverse Agonist", European Journal of Pharmacology, 482, (2003), pp. 139-150.
2000 American Chemical Society, J. Med. Chem., Stevens jm0000665 Supporting Info, pp. 1-14.
W. Schmidt, Ph.D., "Alvimopan* (ADL 8-2698) Is A Novel Peripheral Opioid Antagonist", The American Journal of Surgery, 182, (Suppl to Nov. 2001), pp. 27S-38S.
P. Portoghese, et al., "Binaltorphimine and Nor-Binaltorphimine, Potent and Selective κ-Opioid Receptor Antagonists", Life Sciences, vol. 40, pp. 1287-1292.
Journal of Medicinal Chemistry, vol. 26, No. 10, Oct. 1983, pp. 1341-1343.
C. Mitch, et al., "3,4-Dimethyl-4-(3-hydroxyphenyl)piperidines: Opioid Antagonists with Potent Anorectant Activity", J. Med. Chem., 36, 1993, pp. 2842-2850.
A. Meyers, et al., "Detonation Associated with Oxidations of Tetrahydropyranyl Ether Derivatives. A Serious Note of Caution", Tetrahedron Letters, No. 28, 1976, pp. 2417-2418.
A. Hashimoto, et al., "Probes for Narcotic Receptor Mediated Phenomena. Part 28: New Opioid Antagonist from Enantiomeric Analogues of 5-(3-Hydroxyphenyl)-N-phenylethylmorhan", Bioorganic & Medicinal Chemistry, 10, (2002), pp. 3319-3329.
R. Jones, et al., "Mutational Evidence for a Common κ Antagonist Binding Pocket in the Wild-Type κ and Mutant µ[K303E]Opioid Receptors", Journal of Medicinal Chemistry, vol. 41, No. 25, Dec. 3, 1998, pp. 4911-4914.
R. Jones, et al., "5'-Guanidinonaltrindole, a Highly Selective and Potent κ-Opioid Receptor Anatagonist", European Journal of Pharmacology, 396, (2000), pp. 49-52.

(Continued)

Primary Examiner—Zinna N Davis
(74) Attorney, Agent, or Firm—Oblon, Spivak, McClelland, Maier & Neustadt, P.C.

(57) ABSTRACT

Compounds which bind to opioid receptors are provided. In a preferred embodiment of the invention, the compounds are opioid receptor antagonists. The present invention also provides methods of treating conditions which are mediated by an opioid receptor.

15 Claims, 5 Drawing Sheets

OTHER PUBLICATIONS

M. Kreek, et al., "Pharmacotherapy of Addictions", Nature Publishing Group, vol. 1, Sep. 2002, pp. 710-726.

A. Casy, et al., "Stereochemical Studies of the 4-Alkyl-4-Arylpiperidine Class of Opioid Ligand", Magnetic Resonance in Chemistry, vol. 27, 1989, pp. 964-972.

F. Ivy Carroll, et al., "Pharmacological Properties of JDTic: A Novel κ-Opioid Receptor Antagonist", European Journal of Pharmacology, 501, (2004), pp. 111-119.

2003 American Chemical Society, J. Med. Chem., Stevens jm030419a Supporting Info, pp. 1-10.

A. Casy, et al., "Stereochemical Influences Upon the Opioid Ligand Activites of 4-Alkyl-4-Arylpiperidine Derivatives", Chirality, vol. 1, 1989, pp. 202-208.

Adolor Corporation, News Releases, pp. 1-4.

D. Abraham, Burger's Medicinal Chemistry and Drug Discovery, 6th Ed., vol. 6: Nervous System Agents, Chapter 7: Narcotic Analgesics, pp. 329-481.

6a, R = CH₃, X = Y = H b, R = C₆H₂(CH₂)₂, X = Y = H c, R = C₆H₅(CH₂)₃, X = Y = H

Reagents: (a) s-$C_4H_9Li$, THF; (b) $Br(CH_2)_4Cl$, $(C_2H_5)_2O$; (c) NaI, $CH_3CN$; (d) $NaBH_4$, $C_2H_5OH$; (e) HBr, HOAc Reagents: (a) ACE-Cl, (ClCH$_2$)$_2$; (b) CH$_3$OH, reflux; (c) C$_6$H$_5$CH$_2$CHO, NaB(OAc)$_3$H, (ClCH$_2$)$_2$; (d) HBr, HOAc

Figure 5

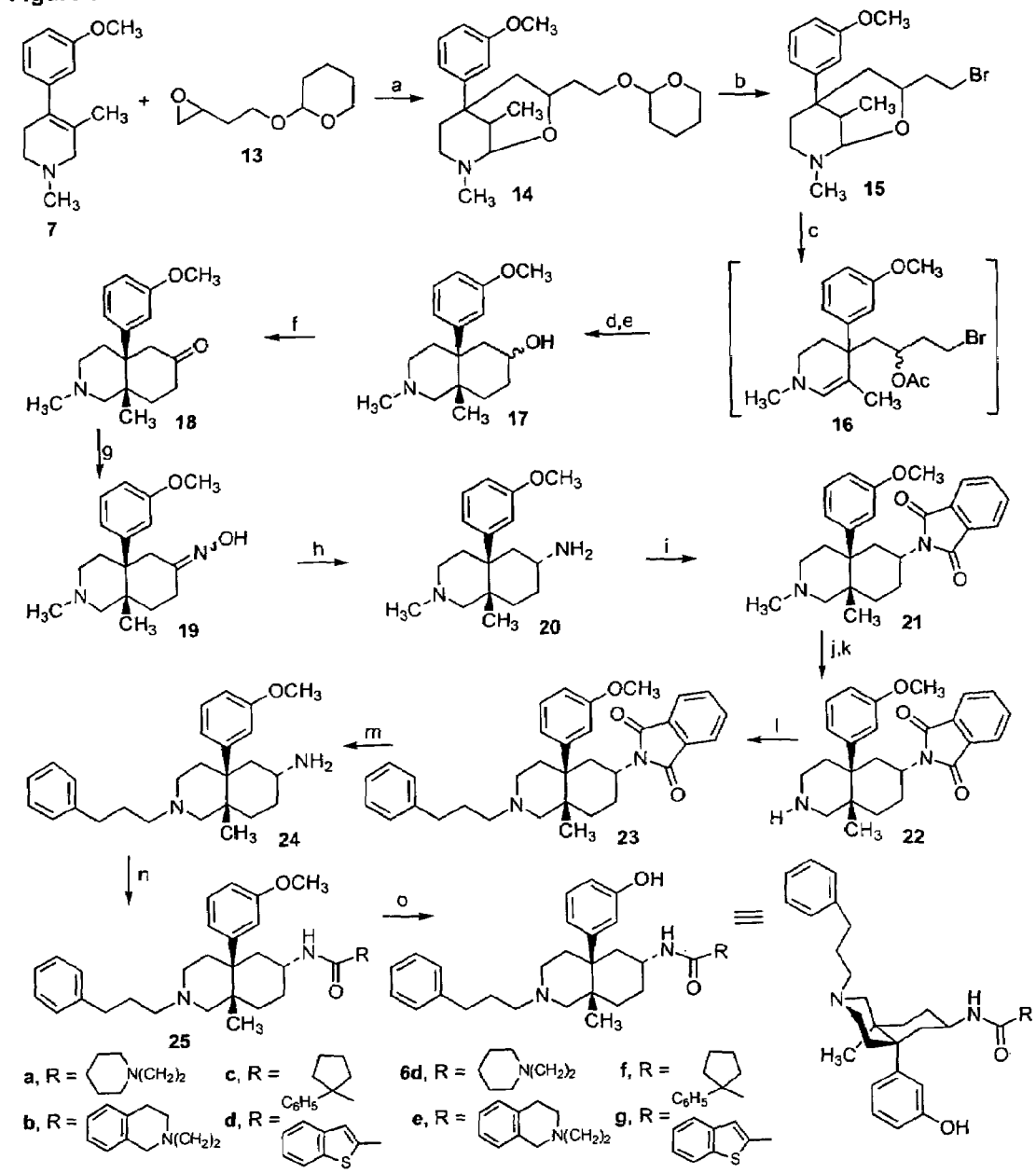

a Reagents and conditions: (a) s-BuLi, THF, -10 °C to 0 °C (1.5 h), 70%; (b) (C6H5)3P, Br2, THF, 0 °C to room temperature (12 h), 70%; (c) TFA, Ac2O, room temperature (1 h); (d) K2CO3, CH3CN, reflux (3 h); (e) NaBH4, CH3OH, 0 °C to room temperature (36 h), 70%; (f) oxalyl chloride, DMSO, -70 °C to room temperature (1 h), 92%; (g) NH2OH·HCl, absolute EtOH, reflux (5 h), 96%; (h) Na, (CH3)2CHOH, toluene, reflux (12 h), 94%; (i) phthalic anhydride, toluene, reflux (12 h), 90%; (j) ACE-Cl, 1,2-dichloroethane, reflux (5 h); (k) CH3OH, reflux (12 h), 99%; (l) hydrocinnamaldehyde, NaBH(OAc)3, 1,2-dichloroethane, room temperature, 87%; (m) N2H4 hydrate, EtOH, reflux (12 h), 97%; (n) appropriate acid, BOP reagent, TEA, THF, room temperature (2 h), ~90%; (o) BBr3, CH2Cl2, -78 °C to room temperature (1.5 h). [N.B.: All indicated configurations are relative stereochemistry.]

OCTAHYDROISOQUINOLINE COMPOUNDS AS OPIOID RECEPTOR MODULATORS

BACKGROUND OF THE INVENTION

1. Field of the Invention

The present invention relates to compounds which bind to opioid receptors. In a preferred embodiment of the invention, the compounds are opioid receptor antagonists. The present invention also provides methods to treat conditions which are mediated by an opioid receptor.

2. Description of the Background

The opioid receptor system has been extensively investigated, and thousands of compounds have been synthesized and evaluated in radioligand binding assays, tissue assays, and animal models.[1] Numerous structural types of opioid agonists have been discovered, and several such as methadone, meperidine, fentanyl, and pentazocine as well as others have become important drugs for the treatment of pain.[1] In contrast, there are only a few structural types that show potent, opioid pure antagonist activity.[1] The demonstrated effectiveness of opioid antagonists for the treatment of other substances of abuse as well as potential use in treatment of obesity depression and other CNS disorders has spurred new interest in the development of novel antagonists for opioid receptors.[1,2]

Mounting evidence suggests that the endogenous kappa opioid system is involved in stress, depression, and other CNS disorders. Since stress and depression are both involved in relapse to substance abuse (cocaine, heroin, methamphetamine, nicotine, and alcohol) kappa antagonists will be useful in treating substance abuse relapse. In addition, the fact that the endogenous kappa opioid system opposes the actions of mu agonists suggests that antagonists selective for the kappa receptor system could suppress or eliminate the symptoms of withdrawal, which arise from an overactive kappa receptor system and thus could promote abstinence and prevent relapse. Therefore, the development of novel kappa antagonists possessing improved pharmacokinetic profiles would be of great value.

The oxymorphone-related compounds such as naloxone (1a) and naltrexone (1b) (FIG. 1), where the antagonist activity is dependent upon the N-substituent, have received considerable attention over the past few decades.[1] Naloxone (1a) is used as an approved drug to treat heroin overdose and to reverse respiratory depression caused by morphine.[2] Naltrexone (1b) is used to treat heroin and alcohol abuse.[1] Pioneering studies by Portoghese and coworkers lead to the development of the prototypical kappa and delta opioid receptor antagonists, naltrindole (2, NTI), norbinaltorphimine (3, nor-BNI), and GNTI (4).[5-6] More recently, we discovered the selective kappa opioid receptor antagonist JDTic (5), which is derived from the N-substituted trans-3,4-dimethyl-(3-hydroxyphenyl)piperidine class of pure antagonist.[7-13]

Zimmerman et al. reported that trans-4a-aryldecahydroisoquinoline analogs possessed high affinity for the μ and κ opioid receptors and were potent analgesics in animal assays.[14] The effect of varying the N-substituent in the trans-4a-aryldecahydroisoquinoline paralleled, to a certain extent, previous findings with other morphine part structures. Replacement of N-methyl with a phenethyl group significantly increased analgesic potency. The N-cyclopropylmethyl analogue was found in rodents to have mixed agonist-antagonist properties; however, its antagonist activity was far weaker than those reported for the N-(cyclopropylmethyl) morphinan and benzomorphan derivatives. In this application, we present methods to synthesize N-substituted 4a-(3-hydroxyphenyl)-8a-methyloctahydroisoquinolines and present test data that show these compounds to be potent opioid pure antagonists.

SUMMARY OF THE INVENTION

It is an object of the present invention to provide compounds which modulate the activity of opioid receptors.

It is an object of the present invention to provide opioid receptor antagonists.

It is still another object of the invention to provide methods of treating conditions which are mediated by an opioid receptor.

The objects of the present invention and others may be accomplished with compounds of the formula:

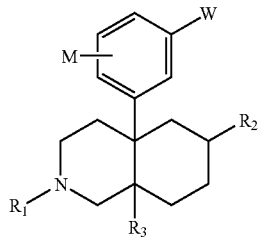

where

M is hydrogen, halogen, $C_1$-$C_4$ alkyl, CN, $OC_{1-8}$ alkyl, $OC_{3-8}$ alkenyl, $OC_{3-8}$ alkynyl, or $OC_{1-8}$ alkylaryl;

$R_1$ is $C_{1-8}$ alkyl, $C_{3-8}$ alkenyl, $C_{3-8}$ alkynyl, $C_{1-8}$ alkylaryl,

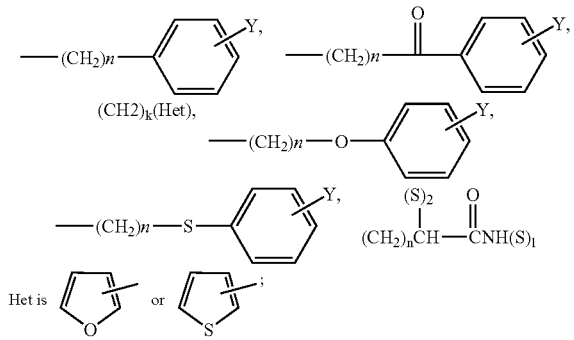

$(S)_1$ is hydrogen, $CH_2CO_2H$, $CH_2CO_2CH_3$, or $CH_2CO_2C_2H_5$;

$(S)_2$ is hydrogen, $CH_3$, $C_2H_3$, $CH_2C_6H_5$, or $CH_2CH_2C_6H_5$;

$R_2$ is =O, hydrogen, $NR_7R_8$,

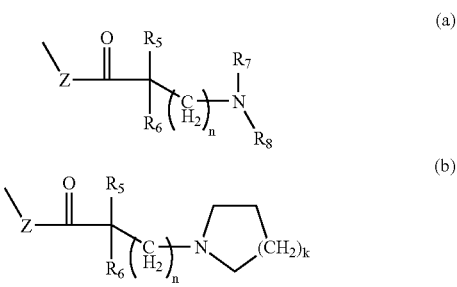

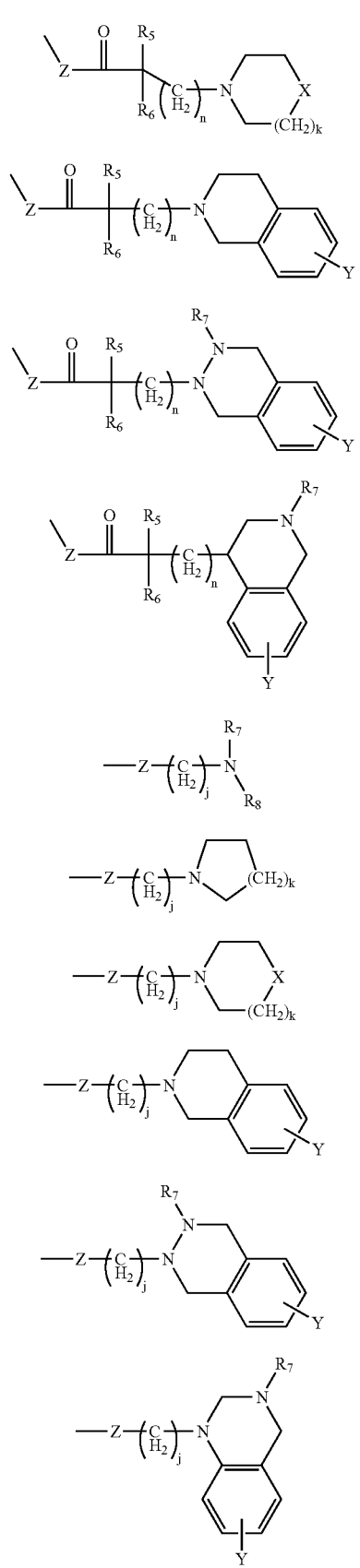
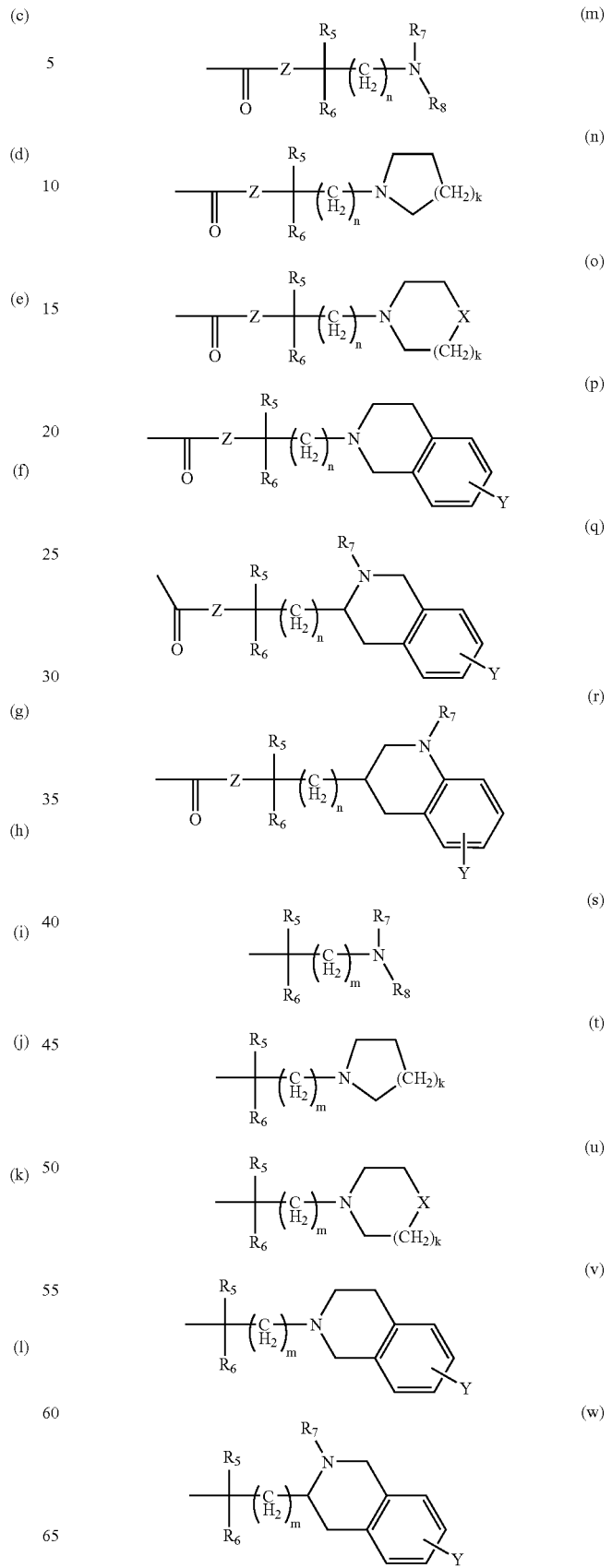

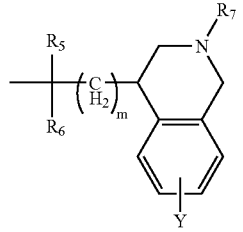 (x)
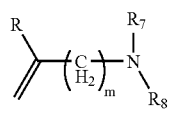 (y)
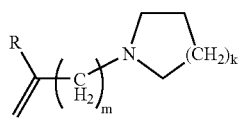 (z)
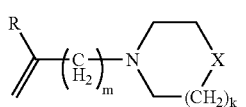 (aa)
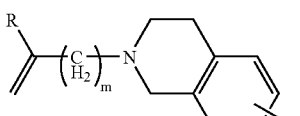 (bb)
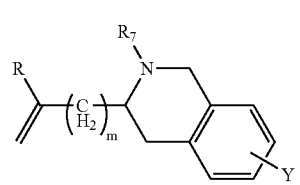 (cc)
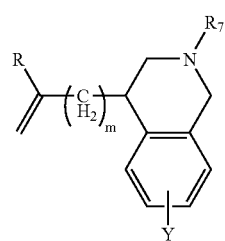 (dd)
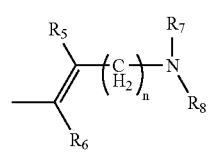 (ee)
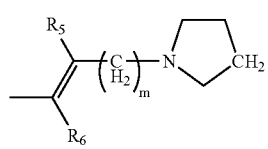 (ff)
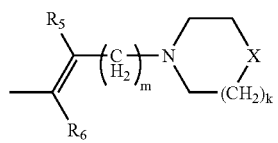 (gg)
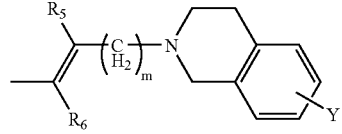 (hh)
(ii)
(jj)
 (kk)
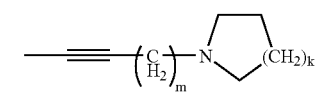 (ll)
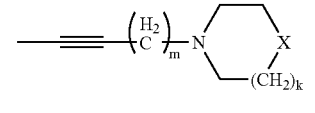 (mm)
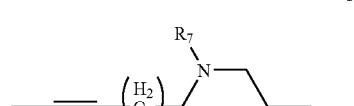 (nn)
(oo)
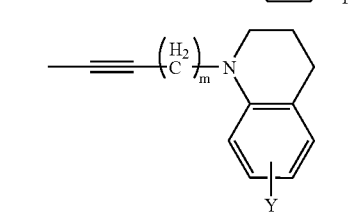 (pp)
X is NR, O, or S;
Y is OH, OR$_9$, C$_{1-8}$ alkyl, F, Cl, Br, CF$_3$, or CN;
R is hydrogen, C$_{1-8}$ alkyl, C$_{3-8}$ alkenyl, C$_{3-8}$ alkynyl, C$_{1-8}$ alkylaryl, or CO$_2$R$_9$
W is hydrogen, OH, OCOR$_9$, N(R$_4$)$_2$, NR$_3$SO$_2$R$_9$, NR$_3$COR$_9$, NR$_3$CO$_2$R$_9$, CONH$_2$, or NHCHO;
Z is NR$_3$, O, or S;
n is 1, 2, or 3;

m is 1, 2, 3, or 4;
j is 2, 3, or 4;
k is 1 or 2;
each $R_3$ is, independently, $C_{1-3}$ alkyl, $C_{3-8}$ alkenyl, $C_{3-8}$ alkynyl, $C_{1-8}$ alkylaryl, $CH_2Y$, or $CO_2R$;
each $R_4$ is, independently, hydrogen, $C_{1-8}$ alkyl, $C_{3-8}$ alkenyl, $C_{3-8}$ alkynyl, or $C_{1-8}$ alkylaryl;
$R_5$ and $R_6$ are each, independently, hydrogen, $C_{1-8}$ alkyl, $C_{3-8}$ alkenyl, $C_{3-8}$ alkynyl, $C_{1-8}$ alkylcycloalkyl, or $C_{1-8}$ alkylaryl;
$R_7$ and $R_8$ are each, independently, hydrogen, $C_{1-8}$ alkyl, $C_{3-8}$ alkenyl, $C_{3-8}$ alkynyl, $C_{1-8}$ alkylcycloalkyl, or $C_{1-8}$ alkylaryl;
$R_9$ is $C_{1-8}$ alkyl, $C_{3-8}$ alkenyl, $C_{3-8}$ alkynyl, or $C_{1-8}$ alkylaryl,
or a pharmaceutically acceptable salt thereof.

The objects of the present invention may also be accomplished with a pharmaceutical composition, comprising the compound described above and a pharmaceutically acceptable carrier or diluent.

The objects of the present invention may also be accomplished with a method of treating a condition mediated by an opioid receptor, comprising administering an effective amount of the compound described above to a subject in need thereof.

BRIEF DESCRIPTION OF THE FIGURES

FIG. 5: synthetic route to exemplary opioid antagonists 6d-6g of the present invention

DETAILED DESCRIPTION OF THE INVENTION

Figure 1:
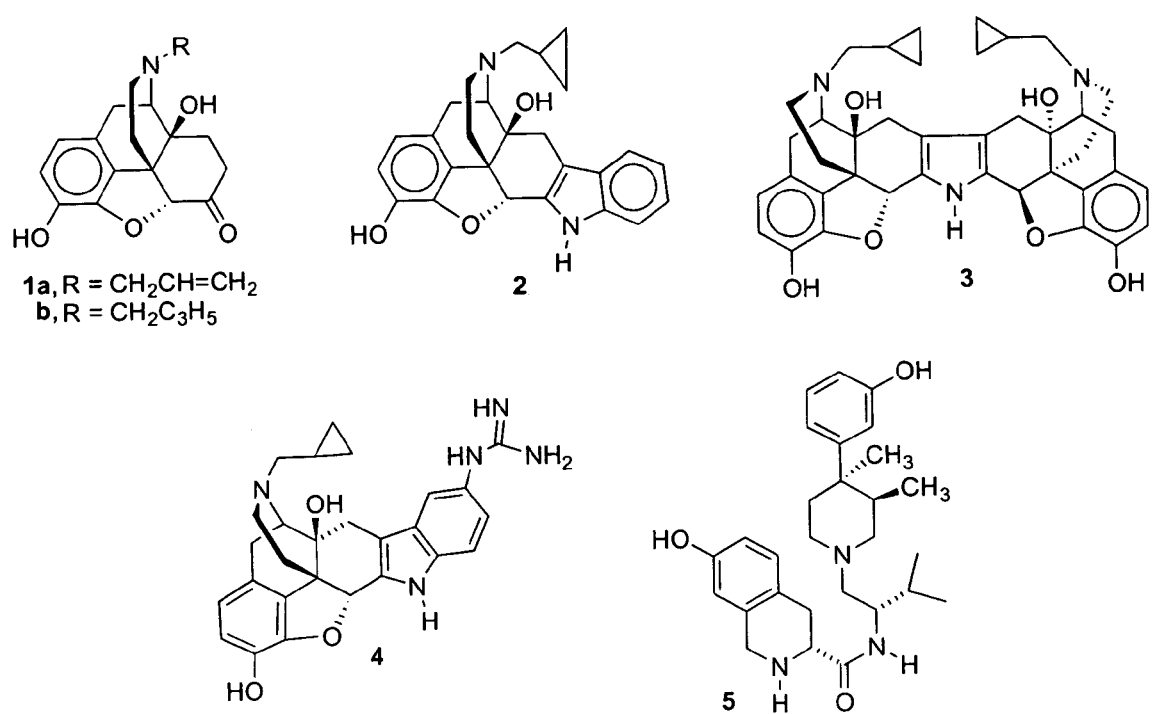
FIG. 1: structures of reference opioid antagonists

The present invention provides compounds which affect the activity of opioid receptors. These compounds are represented by the general formula:

wherein
M is hydrogen, halogen, $C_1$-$C_4$ alkyl, CN, $OC_{1-8}$ alkyl, $OC_{3-8}$ alkenyl, $OC_{3-8}$ alkynyl, or $OC_{1-8}$ alkylaryl;
$R_1$ is $C_{1-8}$ alkyl, $C_{3-8}$ alkenyl, $C_{3-8}$ alkynyl, $C_{1-8}$ alkylaryl, $(S)_1$ is hydrogen, $CH_2CO_2H$, $CH_2CO_2CH_3$, or $CH_2CO_2C_2H_5$;
$(S)_2$ is hydrogen, $CH_3$, $C_2H_3$, $CH_2C_6H_5$, or $CH_2CH_2C_6H_5$;
$R_2$ is =O, hydrogen, $NR_7R_8$, -continued

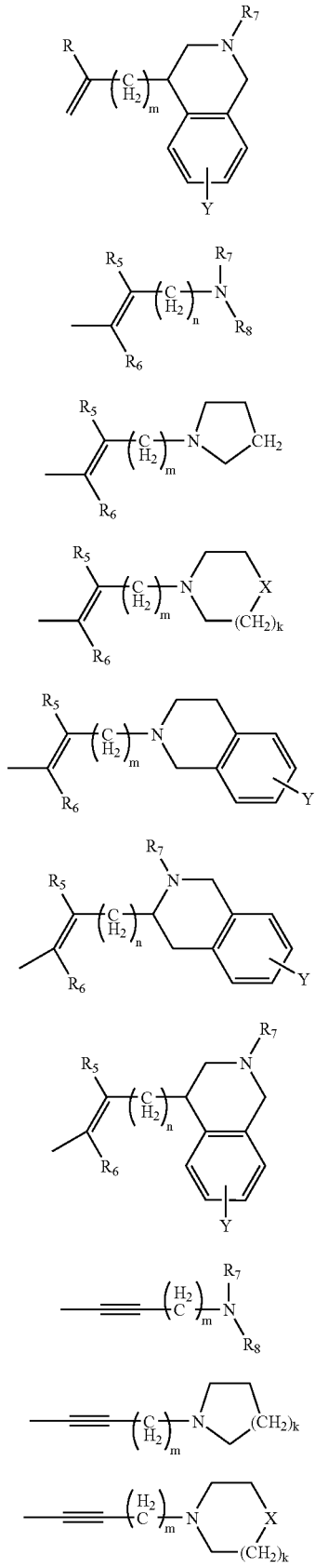

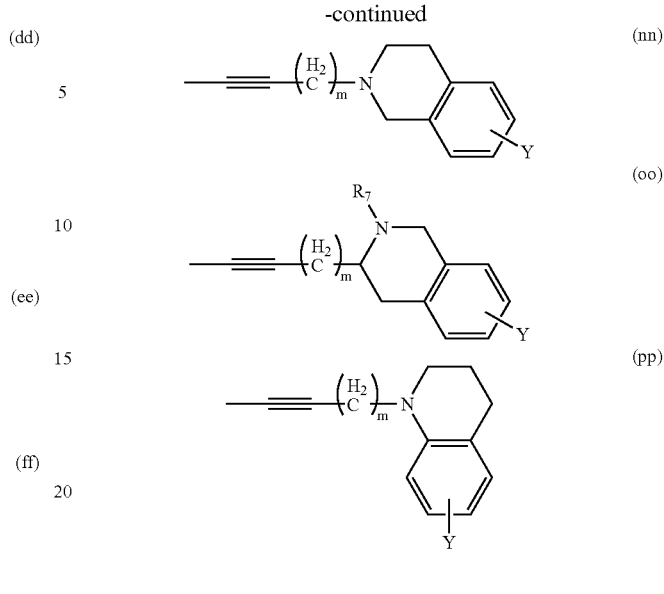

X is NR, O, or S;
Y is OH, OR$_9$, C$_{1-8}$ alkyl, F, Cl, Br, CF$_3$, or CN;
R is hydrogen, C$_{1-8}$ alkyl, C$_{3-8}$ alkenyl, C$_{3-8}$ alkynyl, C$_{1-8}$ alkylaryl, or CO$_2$R$_9$
W is hydrogen, OH, OCOR$_9$, N(R$_4$)$_2$, NR$_3$COR$_9$, NR$_3$SO$_2$R$_9$, NR$_3$CO$_2$R$_9$, CONH$_2$, or NHCHO;
Z is NR$_3$, O, or S;
n is 1, 2, or 3;
m is 1, 2, 3, or 4;
j is 2, 3, or 4;
k is 1 or 2;
each R$_3$ is, independently, C$_{1-3}$ alkyl, C$_{3-8}$ alkenyl, C$_{3-8}$ alkynyl, C$_{1-8}$ alkylaryl, CH$_2$Y, or CO$_2$R;
each R$_4$ is, independently, hydrogen, C$_{1-8}$ alkyl, C$_{3-8}$ alkenyl, C$_{3-8}$ alkynyl, or C$_{1-8}$ alkylaryl;
R$_5$ and R$_6$ are each, independently, hydrogen, C$_{1-8}$ alkyl, C$_{3-8}$ alkenyl, C$_{3-8}$ alkynyl, C$_{1-8}$ alkylcycloalkyl, or C$_{1-8}$ alkylaryl;
R$_7$ and R$_8$ are each, independently, hydrogen, C$_{1-8}$ alkyl, C$_{3-8}$ alkenyl, C$_{3-8}$ alkynyl, C$_{1-8}$ alkylcycloalkyl, or C$_{1-8}$ alkylaryl.
R$_9$ is C$_{1-8}$ alkyl, C$_{3-8}$ alkenyl, C$_{3-8}$ alkynyl, or C$_{1-8}$ alkylaryl,
or a pharmaceutically acceptable salt thereof.

As used throughout this disclosure, the terms "alkyl group" or "alkyl radical" encompass all structural isomers thereof, such as linear, branched and cyclic alkyl groups and moieties, and mixed structures thereof (e.g., cyclopropyl-CH$_2$—). Unless stated otherwise, all alkyl groups described herein may have 1 to 8 carbon atoms, inclusive of all specific values and subranges therebetween, such as 2, 3, 4, 5, 6, or 7 carbon atoms.

As used herein, the term "alkylaryl group" refers to an aryl moiety bonded to an alkyl radical. The aryl moiety may have 6 to 20 carbon atoms. The aryl moiety may contain only carbon and hydrogen atoms. Alternatively, the aryl moiety may contain heteroatoms, for example 1, 2, or 3 heteroatoms (e.g., oxygen, nitrogen, and sulfur). A particularly preferred aryl moiety is phenyl-. The alkyl radical of the alkylaryl group may be as described above. The alkyl group or moiety and/or the aryl moiety may be substituted. Suitable substituents include halogens (F, Cl, Br and I), alkyl groups (e.g., C$_1$-C$_8$), alkenyl groups (e.g., C$_2$-C$_8$), alkoxy groups (e.g., C$_1$-C$_8$ alkoxy groups), hydroxy, —CF$_3$, —CN, —NH$_2$, —NHR, or —N(R$_a$)$_2$. The R$_a$ groups are, independently, an alkyl group (such as described above), an aryl group (such as phenyl) or an alkylaryl group (such as benzyl). Alternatively, the R$_a$ groups may, together, form a cyclic alkyl group. Such a cyclic alkyl group may, preferably, contain 2 to 8 carbon atoms, with 4 or 5 carbon atoms particularly preferred.

The alkenyl group or alkynyl group may have one or more double or triple bonds, respectively. As will be readily appreciated, when an alkenyl or alkynyl group is bonded to a heteroatom a double or triple bond is not formed with the carbon atom bonded directly to the heteroatom.

The aryl group is a hydrocarbon aryl group, such as a phenyl, naphthyl, phenanthryl, anthracenyl group, which may have one or more C$_{1-4}$ alkyl group substituents. The aryl moiety of the aryl-C$_{1-8}$ alkyl group is preferably a phenyl group. The phenyl group may be unsubstituted or may be substituted with one or more of the substituents described above. The C$_{1-8}$ alkyl moiety of the aryl-C$_{1-8}$ alkyl group may be unsubstituted or substituted with one or more of the substituents described above or keto, i.e., 2 hydrogens on a carbon atom are replaced by =O. The substituent, when present, is preferably at the beta or gamma carbon atom and/or alpha to the aryl moiety.

Figure 2:
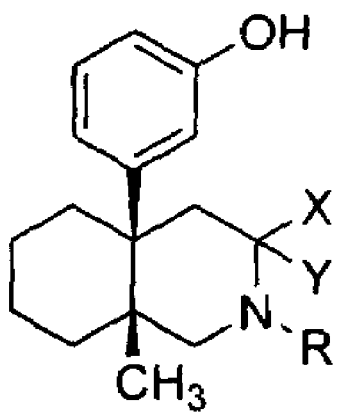
FIG. 2: structures of exemplary opioid antagonists of the present invention
Figure 2:
Figure 2:
Figure 2:
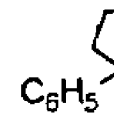
Figure 2:

FIG. 2 shows the structure of representative examples of compounds within the scope of the present invention. In one embodiment, M is hydrogen, C$_1$-C$_4$ alkyl, or OC$_{1-8}$ alkyl;
R$_1$ is C$_{1-8}$ alkyl or C$_{1-8}$ alkylaryl;
R$_2$ is =O, hydrogen, or NR$_7$R$_8$;
W is hydrogen or OH; and
R$_3$ is C$_{1-3}$ alkyl.

In another embodiment, the compound is represented by the formula:

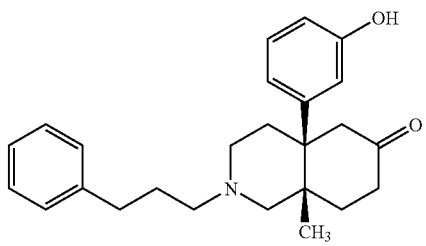

In another embodiment, the compound is represented by the formula:

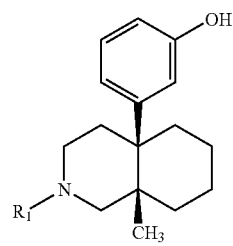

where R is CH$_3$, C$_6$H$_5$(CH$_2$)$_2$ or C$_6$H$_5$(CH$_2$)$_3$.

In another embodiment, the compound is represented by the formula:

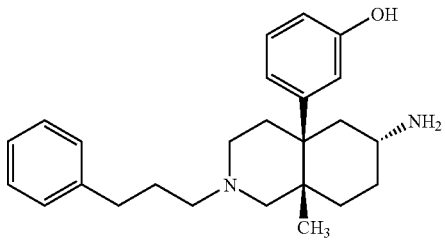

In another embodiment, the compound is represented by the formula:

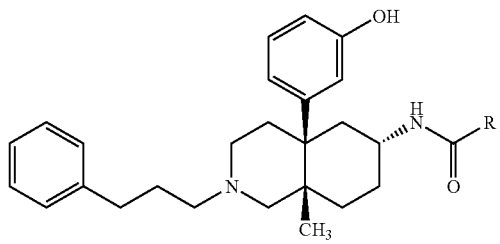

where R is

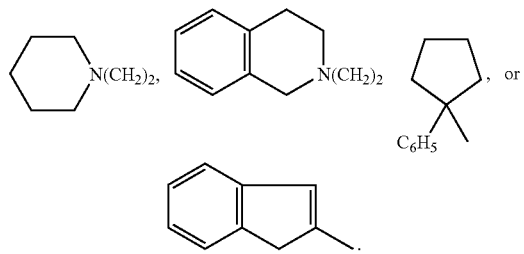

In one embodiment, the substituents on the ring are cis.

In another embodiment, W is NH$_2$, NHC$_{1-8}$ alkyl, or W is N(R$_4$)$_2$, and each R$_4$ therein is, independently, a C$_{1-8}$ alkyl group.

The compounds of the present invention are opiates which are preferably antagonists that are selective for the kappa receptor. The kappa/mu selectivity may be at least 2:1, but is preferably higher, e.g., at least 5:1, 10:1, 25:1, 50:1, 100:1 or 200:1. The kappa/delta selectivity may be at least 2:1, but is preferably higher, e.g., at least 5:1, 10:1, 25:1, 50:1, 100:1, 200:1, 250:1 or 500:1.

Figure 3:
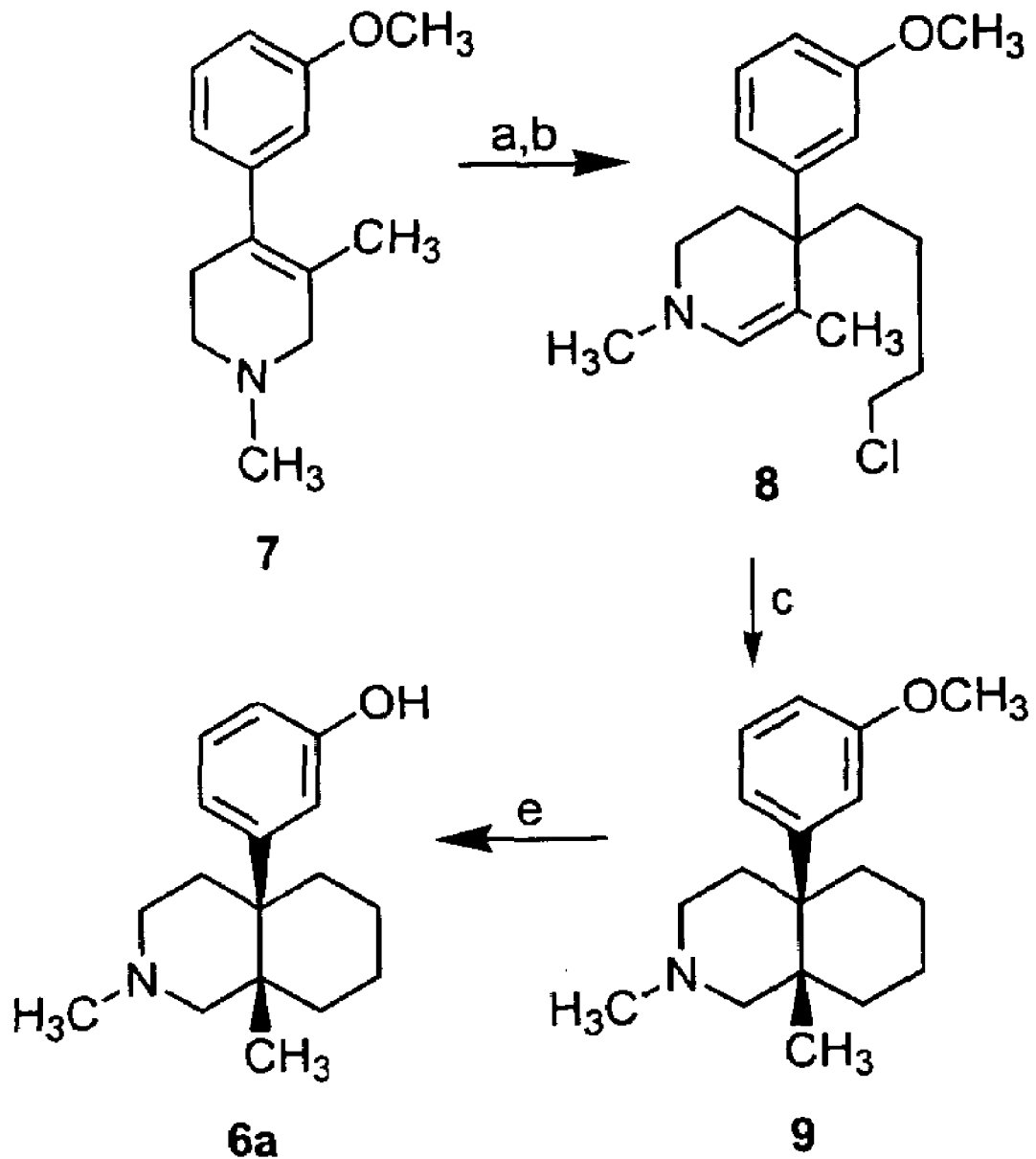
FIG. 3: exemplary opioid antagonists 6a of the present invention
Figure 4:
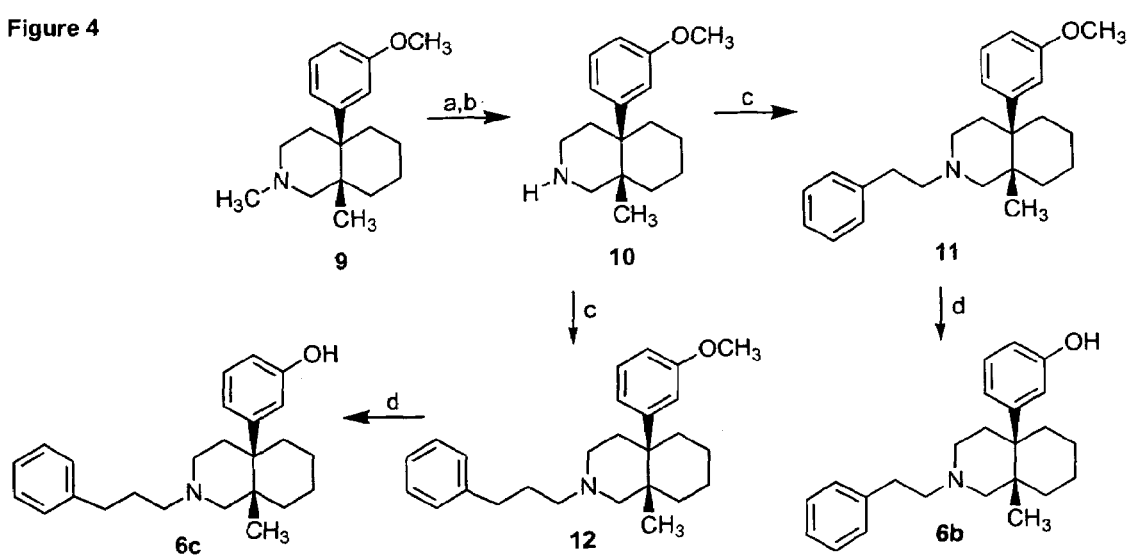
FIG. 4: synthetic route to exemplary opioid antagonists 6b and 6c of the present invention

The compounds of the present invention may be synthesized, for example, in accordance with the reaction sequence shown in FIGS. 3-5.

Pharmaceutical salts of compounds according to the present invention are an important aspect. Pharmaceutical salts of compounds can be obtained by forming salts with any acidic or basic group present on a compound. Examples of pharmaceutically acceptable salts of the compounds are the salts of hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid, mandelic acid, sodium, potassium, magnesium, calcium, and lithium. Mesylate and/or citrate salts may be particularly preferred.

As noted above, the compounds may have optical centers and therefore may occur in different enantiomeric and other stereoisomeric configurations. The invention includes all enantiomers, diastereomers, and other stereoisomers of the compounds discussed above, as well as racemic and other mixtures thereof.

The present invention also includes isotopically-labeled compounds, which are identical to those described above, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, iodine, and chlorine, such as $^3$H, $^{11}$C, $^{14}$C, $^{18}$F, $^{76}$Br, $^{123}$I, and $^{125}$I. Compounds of the invention and pharmaceutically acceptable salts of the compounds that contain the aforementioned isotopes and/or other isotopes of other atoms are within the scope of this invention. Isotopically labeled compounds of the invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. $^{11}$C, $^{18}$F, and $^{76}$Br isotopes are particularly useful in PET (positron emission tomography), and $^{125}$I, isotopes are particularly useful in SPECT (single photon emission computerized tomography), all useful in brain imaging. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds can generally be prepared by carrying out the procedures described above, by substituting a readily available isotopically labeled reagent for a non-isotopically labeled reagent.

Accordingly, the present invention also provides a compound of wherein one or more atoms thereof have an atomic mass or mass number different from the atomic mass or mass number usually found in nature, or a pharmaceutically acceptable salt of such compound. The invention also provides a method for obtaining an image of opioid receptors in a mammalian, including a human, subject which method comprises administering to the subject an amount of an isotopically-labeled compound or pharmaceutically acceptable salt thereof, effective in imaging opioid receptors in the subject.

The compounds of the invention may be administered alone or in combination with pharmaceutically acceptable carriers, in either single or multiple doses. Suitable pharmaceutical carriers include inert solid diluents or fillers, sterile aqueous solutions and various organic solvents. The pharmaceutical compositions formed by combining a compound or a pharmaceutically acceptable salt thereof can then be readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing a compound of this invention or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

A compound or a pharmaceutically acceptable salt thereof can be administered orally, transdermally (e.g., through the use of a patch), parenterally (e.g. intravenously), rectally, topically, or by inhalation. In general, the daily dosage for treating a disorder or condition as described herein using a compound will be about from about 0.01 to about 100 mg per kg, preferably from about 0.1 to about 10 mg per kg, of the body weight of the animal to be treated. As an example, a compound or a pharmaceutically acceptable salt thereof can be administered for treatment to an adult human of average weight (about 70 kg) in a dose ranging from about 0.5 mg up to about 10 g per day, preferably from about 1 mg to about 1 g per day, in single or divided (i.e., multiple) portions. Variations based on the aforementioned dosage ranges may be made by a physician of ordinary skill taking into account known considerations such as the weight, age, and condition of the animal being treated, the severity of the affliction, and the particular route of administration chosen.

The compounds of the present invention may be used to bind opioid receptors. Such binding may be accomplished by contacting the receptor with an effective amount of the inventive compound. Of course, such contacting is preferably conducted in a aqueous medium, preferably at physiologically relevant ionic strength, pH, etc.

The present invention also provides a method for treating a subject in need thereof, having a disease state, disorder or condition selected from irritable bowel syndrome; constipation; nausea; vomiting; pruritic dermatoses, for example allergic dermatitis or contact dermatitis; psoriasis; eczema; an insect bite; an eating disorder, for example anorexia, bulimia, or obesity; depression, anxiety, schizophrenia; drug addiction, for example alcohol addiction, amphetamine addiction, cocaine addiction and addiction to an opioid, for example morphine, opium, or heroin; an opioid overdose; a sexual dysfunction, for example erectile dysfunction or impotence; stroke; head trauma; traumatic brain injury; spinal damage; Parkinson's disease; Alzheimer's disease, age-related cognitive decline; and Attention Deficit and Hyperactivity Disorder; which method comprises administering to the subject an amount of a compound or a pharmaceutically acceptable salt thereof as described above effective in treating the disease state, disorder or condition in the subject.

The subject to be treated may be a human or a non-human animal, preferably a mammal. Examples of suitable non-human animals include dogs, cats, sheep, pigs, cows and horses.

Assays which may be used for determining the binding of compounds according to the present invention to opioid receptors are well known in the art. These assays may be used to assess the ability of a compound to modulate (i.e., inhibit, partially inhibit, activate or partially activate) an opioid receptor or receptors by determining a compound's agonist or antagonist activity in the in vitro or in vivo assay. These assays include, for example, the GTP gamma S binding assay as described in Martin, et al., J. Pharm. Exp. Ther., 301, 661-671 (2003) and Zaki, et al., J. Pharm. Exp. Ther., 298, 1015-1020 (2002), as well as other binding assays, such as the isolated guinea pig ileum and receptor binding assay as disclosed, for example, by Takayama, et al., J. Med. Chem., 45, 1949-1956 (2002) and the guinea pig brain binding assay as described by Wentland, et al., J. Med. Chem., 46, 838-849 (2003). The use of mouse brain tissue to determine the functional activity of the compounds of interest is another binding assay which can be used for characterizing the modulation of the present compounds at opioid receptors, as disclosed by Martin, et al., Idem. Other binding assays include the tail-flick assay in mice or the radiant heat paw-withdrawal hyperalgesic testing in mice, as described by Hosohata, et al., J. Pharm. Exp. Ther., 304, 683-688 (2003), among others. These assays or variations of these assays are well-known to those of ordinary skill in the art. Each of the references cited above are incorporated herein by reference.

Chemistry

N-Substituted cis-8a-methyl-4a-(3-hydroxyphenyl)octahydroisoquinolines (6a-c) were synthesized from tetrahydropyridine (7)[12] as outlined in FIGS. 3-4. Deprotonation of 7 with sec-butyl lithium in tetrahydrofuran at −78° C. provided the metalated enamine, which was added to an ethereal solution of 1-bromo-4-chlorobutane to give the endocyclic enamine 8. Without isolation this material was treated with sodium iodide in acetonitrile at reflux followed by reduction with sodium borohydride in ethanol to give the octahydroisoquinoline methyl ether 9. O-Demethylation of 9 with refluxing 48% hydrogen bromide provided the desired 6a. Single crystal X-ray analysis of the hydrochloride salt of 6a showed that the 4a-(3-hydroxyphenyl) group and the 8a-methyl group were cis to one another and that the 4a-(3-hydroxyphenyl) group was in the equatorial conformation.

The N-phenethyl and N-phenpropyl 4a-(3-hydroxyphenyl)-8a-methyloctahydroisoquinolines (6b and 6c) were prepared starting with 9 according to the method illustrated in FIG. 4. Treatment of 9 with 1-chloroethyl chloroformate (ACE-Cl) followed by refluxing the resulting product in methanol afforded the N-demethylated product 10. Reductive amination of 10 with phenylacetaldehyde or hydrocinnamaldehyde using sodium triacetoxyborohydride as the reducing agent afforded the N-phenethyl and N-phenpropyl methyl ether intermediates 11 and 12, respectively. Treatment of 11 and 12 with refluxing 48% hydrobromic acid in acetic acid provided the desired products 6b and 6c.

The acylamino N-phenethyl-4a-(3-hydroxyphenyl)-8a-methyloctahydroisoquinoline analogues 6d-g were synthesized as outlined in FIG. 5. Deprotonation of 7 with sec-butyl lithium in tetrahydrofuran at −10 to 0° C. provided the metalated imine, which was added to an ethereal solution of tetrahydro-(2-oxiranylethoxy)-2H-pyran (13) to provide the intermediate 14. Addition of bromine to a tetrahydrofuran solution of 14 and triphenylphosphine yielded the bromo compound 15. Treatment of 15 with a mixture of acetic and trifluoroacetic anhydride afforded the bromo acetoxy intermediate 16. An acetonitrile solution of 16 containing potassium carbonate was refluxed for 3 h to affect both cyclization and hydrolysis of the acetate. Reduction with sodium borohydride afforded the 6-hydroxyoctahydroisoquinoline 17. Swern (Moffatt-Swern) oxidation of 17 using oxalyl chloride and dimethylsulfoxide in methylene chloride gave the keto compound 18. Condensation of 18 with hydroxylamine hydrochloride in ethanol afforded 19 which yielded 20 on reduction using sodium and 2-propanol in refluxing toluene. Refluxing a solution of 20 in toluene with phthalic anhydride yielded the phthalimide 21. N-Demethylation of 21 to 22 was achieved with 1-chloroethyl chloroformate in 1,2-dichloroethane, followed by hydrolysis of the resulting carbamate in refluxing methanol. Reductive alkylation of 22 with hydrocinnamaldehyde using sodium triacetoxyborohydride gave the N-phenylpropyl analogue 23. Single crystal X-ray analysis of 23 showed that similar to 6a.HCl the 4a-(3-hydroxyphenyl) group and the 8a methyl were cis to one another and that the 4a-(3-hydroxyphenyl) group was in the equatorial conformation. In addition, the 6-phthalimide group is positioned in an equatorial conformation and is trans to the equatorial and axially oriented 4a-(3-hydroxyphenyl) and 8a-methyl groups, respectively. Refluxing 23 with hydrazine in ethanol provided the N-phenylpropyl-6-amino compound 24. Coupling of 24 with the appropriately substituted carboxylic acid, using benzotriazol-1-yloxy-tris-(dimethylamino)phosphate (BOP, Castro's reagent) in tetrahydrofuran/triethylamine provided the desired methoxy-protected 6-acylamino compounds 25a-d. O-Demethylation of 25a-d with boron tribromide in methylene chloride at −78° C. provided final products 6d-g.

EXAMPLES

N-Methyl-4a-(3-methoxyphenyl)-8a-methyloctahydroisoquinoline (9). To a dry three-neck round bottomed flask was charged 2.27 g[24] (0.01 mol) of 7 and 50 mL of dry THF. This was cooled to −78° C., and to this was added 11.2 mL (14.6 mmol) s-BuLi (1.3M in cyclohexane) via syringe over 20 min. The flask was warmed to −20° C. and aged for 30 min. The flask was cooled to −78° C. and cannulated into a mixture of 50 mL dry diethyl ether and 5.90 g (0.034 mol) 1-bromo-4-chlorobutane at −50° C. over 20 min. This mixture was aged for 1 h and then quenched with ice-cold 1 N HCl. The contents of the flask were transferred to a separatory funnel with ice-cold ether and ice-cold 1 N HCl. The aqueous layer was removed and stored in an ice bath, while the organic layer was twice extracted with ice-cold 1 N HCl. The combined aqueous layers were placed into a new separatory funnel and extracted twice with ice-cold ethyl ether. The aqueous layer was made basic with 50% NaOH to pH 10. The aqueous layer was extracted 3 times with ice-cold ethyl ether. The ether extracts were dried ($K_2CO_3$), filtered, the solvent removed at 0° C. The resulting residue was dissolved in 40 mL of dry $CH_3CN$, and to this was added 3.91 g (0.027 mol) NaI and 2.89 g (0.021 mol) of $K_2CO_3$. The flask was attached to a reflux condenser and refluxed with stirring for 20 h. The reaction mixture was cooled to room temperature and filtered. The solvent was removed on a rota-evaporator, and the residue dissolved in 100 mL of ethanol. To this mixture was added 3.35 g (0.089 mol) of $NaBH_4$ in one portion and the mixture allowed to stir overnight. On the following day, 1 N HCl was added to the mixture until no further evolution of hydrogen was observed. The mixture was stirred for 10 min and then 50% NaOH and water were added until the mixture was clear and basic. The volatiles were removed on rotaevaporator, and the residue was extracted with methylene chloride. The organic layer was dried over anhydrous $Na_2SO_4$. Removal of solvent on rota-evaporator yielded crude product, which was purified by chromatography on alumina using 15% ethyl acetate/hexane as the eluent, gave 2.1 g (76%) of desired product 9 as almost colorless viscous oil: $^1$H NMR (300 MHz, $CDCl_3$) δ 1.09 [s, 3H], 1.54 [br, 8H], 1.88 [m, 3H], 2.11 [s, 3H], 2.50 [m, 3H], 3.81 [s, 3H], 6.74 [br, 1H], 7.08 [s, 1H], 7.20 [m, 2H]; $^{13}$CNMR (300 MHz, $CDCl_3$) δ 158.1, 127.8, 121.6, 115.9, 109.7, 64.6, 54.7, 46.2, 41.6, 36.5, 35.3, 21.5, 21.2.

This material was used in the next step to prepare 6a.

N-Methyl-4a-(3-hydroxyphenyl)-8a-methyloctahydroisoquinoline (6a) Hydrochloride. To a 25 mL single-necked flask was added 180 mg (0.65 mmol) of 9 and 5 mL of glacial acetic acid and 5 mL of 48% HBr. This mixture was heated under reflux for 18 h and then cooled to room temperature. The pH was then adjusted to 10 with cooling with 50% NaOH. This mixture was extracted 3× with methylene chloride. The organic extracts were dried ($Na_2SO_4$), and concentrated under reduced pressure to give 0.17 g (99%) of crude product as a white solid. Purification by chromatography on alumina using 15% ethyl acetate/hexane gave 0.140 g (83%) of desired product as a crystalline white solid.

This free base was dissolved in MeOH and to this was added 3 equivalent of 1 N HCl in dry ethyl ether to give the hydrochloride salt; mp 291-293° C.; $^1$H NMR (300 MHz, DMSO-$d_6$) δ 0.91 [s, 3H], 1.02 [d, 2H], 1.61-1.29 [m, 6H], 2.28 [s, 1H], 2.57-2.49 [m, 4H], 3.38 [s, 3H], 3.90 [t, 1H], 6.51 [m, 1H], 7.09-6.73 [m, 3H], 9.18 [s, 1H], 9.71 [br s, 1H]; $^{13}$CNMR (300 MHz, DMSO-$d_6$)δ 156.9, 147.5, 128.7, 119.4, 116.3, 113.0, 59.8, 49.9, 43.3, 36.8, 36.6, 34.4, 32.5, 31.3, 24.7, 21.3, 20.5. Anal. ($C_{17}H_{26}ClNO.0.75H_2O$) C, H, N.

4a-(3-Methoxyphenyl)-8a-methyloctahydroisoquinoline (10). To a solution of 430 mg (1.59 mmol) of 9 in anhydrous 1,2-dichloroethane (15 mL) at reflux was added 250 mg (1.75 mmol) of 1-chloethyl chloroformate drop wise. The resulting solution was heated under reflux for 20 h and then cooled to room temperature. The mixture was washed with saturated sodium bicarbonate solution, water, the organic layer evaporated, and the resulting oil dissolved immediately in methanol and refluxed overnight. After cooling to room temperature, the methanol was removed under reduced pressure, and the residue was treated with saturated sodium bicarbonate solution. The mixture was extracted with 3:1, methylene chloride/ THF, and the combined organic extracts were washed once with water. Removal of a solvent provided 0.36 g (89%) of crude 10 as yellow oil: $^1$H NMR (300 MHz, $CDCl_3$) δ 1.04 [s, 3H], 2.45-1.43 [m, 13H], 3.06 [m, 2H], 3.80 [s, 3H], 6.76 [m, 1H], 6.98 [m, 3H]; $^{13}$CNMR (300 MHz, $CDCl_3$) δ 159.0, 128.3, 122.2, 116.9, 110.0, 55.6, 55.5, 43.8, 43.5, 36.4, 35.3, 30.7, 24.4, 22.4, 21.9

This material was used to prepare 6b and 6c without further purification.

N-Phenethyl-4a-(3-methoxyphenyl)-8a-methyloctahydroisoquinoline (11). Phenacetaldehyde 87 mg (0.72 mmol) and 190 mg (0.72 mmol) of 10 were mixed in 1,2-dichloroethane (15 mL) and then treated with sodium triacetoxyborohydride 230 mg (1.08 mmol). The reaction mixture remained cloudy throughout the reaction. The mixture was stirred at room temperature under $N_2$ atmosphere for 2 h. The reaction mixture was quenched by adding saturated $NaHCO_3$, and the product was extracted with EtOAc. The EtOAc extract was dried ($MgSO_4$), and the solvent was evaporated to give 0.25 g (95%) of a light yellow oil. Purification by chromatography on alumina using 10% ethyl acetate/hexane gave 0.23 g (89%) of desired product 11 as colorless clear viscous oil: $^{13}$C NMR (300 MHz, $CDCl_3$) δ 158.9, 129.1, 128.6, 128.1, 126.2, 122.5, 117.1, 109.9, 63.2, 61.1, 55.5, 43.1, 37.4, 36.3, 34.0, 30.7, 22.4, 22.1.

The material was used in the next step without further purification.

N-(3-Phenylpropyl)-4a-(3-methoxyphenyl)-8a-methyl-2-octahydroisoquinoline (12). Hydrocinnamaldehyde 110 mg (0.75 mmol) and 190 mg (0.75 mmol) of 10 were mixed in 1,2-dichloroethane (15 mL) and then treated with sodium triacetoxyborohydride 240 mg (1.12 mmol). The reaction mixture remained cloudy throughout the reaction. The mixture was stirred at room temperature under $N_2$ atmosphere for 2.5 h. The reaction mixture was quenched by adding saturated $NaHCO_3$, and the product was extracted with EtOAc. The EtOAc extract was dried ($MgSO_4$) and the solvent was evaporated to give 0.28 g (99%) of 12 as a light yellow viscous oil. Purification by chromatography on alumina using 5% ethyl acetate/hexane gave 0.22 g (79%) of desired product 12 as colorless clear viscous oil, which was used without further purification to synthesize 6c.

N-Phenethyl-4a-(3'-hydroxyphenyl)-8a-methyloctahydroisoquinoline (6b) Hydrochloride. To a 25 mL single-necked flask was added 230 mg (0.64 mmol) of 11 and 5 mL of glacial acetic acid and 5 mL of 48% HBr. This mixture was heated under reflux for 18 h and then cooled to room temperature. The pH was adjusted to 10 with cooling using 50% NaOH. This mixture was extracted 3× with methylene chloride. The resulting organic extracts were dried ($Na_2SO_4$) and concentrated under reduced pressure to give 0.22 g (98%) of crude product as a white solid. Purification by chromatography on alumina using 20% ethyl acetate/hexane gave 0.18 g (81%) of desired product 6b as a crystalline white solid.

The free base was dissolved in MeOH, and to this was added 3 equivalent of 1 N HCl in dry ethyl ether to give the hydrochloride salt as a white crystalline solid: mp 226-228° C.; $^{13}$CNMR (300 MHz, DMSO-$d_6$) δ 156.9, 147.5, 147.6, 129.0, 128.9, 128.7, 127.1, 119.4, 116.3, 113.0, 57.3, 48.7, 41.2, 36.6, 34.5, 32.4, 29.7, 24.8, 21.3, 20.6. Anal. ($C_{24}H_{32}ClNO.0.5H_2O$) C, H, N.

N-(3-Phenpropyl)-4a-(3-hydroxyphenyl)-8a-methyloctahydroisoquinoline (6c) Hydrochloride. To a 25 mL single-necked flask was added 220 mg (0.59 mmol) of 12 and 5 mL of glacial acetic acid and 5 mL of 48% HBr. This mixture was heated under reflux for 18 h and then cooled to room temperature. The pH was adjusted to 10 with cooling using 50% NaOH. This mixture was extracted 3× with methylene chloride. The resulting organic extracts were dried ($Na_2SO_4$) and concentrated under reduced pressure to give 0.21 g (98%) of crude product as a white solid. Purification by chromatography on alumina using 15% ethyl acetate/hexane gave 0.16 g (76%) of desired product 6c as a crystalline white solid.

This free base was dissolved in MeOH and to this was added 3 equivalents of 1 N HCl in dry ethyl ether to give the hydrochloride salt as a white crystalline solid: mp 262-264° C.; $^1$H NMR ($CDCl_3$) δ 1.13 [s, 3H], 1.28 [d, J=6 Hz, 1H], 1.56 [m, 4H], 2.39-1.82 [m, 4H], 2.5 [m, 4H], 2.92 [m, 4H], 3.35 [m, 3H], 6.62 [d, 1H], 7.21-6.95 [m, 3H], 7.34-7.22 [m, 5H], 9.32 [s, 1H], 9.66 [br s, 1H]. Anal. ($C_{25}H_{34}ClNO.0.5H_2O$) C, H, N.

Tetrahydro-2-(oxiranylethoxy)-2H-pyran (13). To a chilled solution (0° C.) of 3,4-dihydro-2H-pyran (117 g, 1.4 mol) in anhydrous ether (600 mL) were added p-toluensulfonic acid (0.5 g) and 3-buten-1-ol (25.0 g, 0.35 mol). The resulting mixture was stirred at room temperature for 5 h and was then quenched by the addition of concentrated ammonium hydroxide (5 mL) and methanol (50 mL). The solvent was evaporated in vacuo, and ether was added to the residue. The precipitated ammonium p-toluenesulfate was filtered, the filtrate was concentrated, and the crude product was purified by flash column chromatography on silica gel (0-5% ethyl acetate in hexanes) to give 2-(3-butenyloxy)tetrahydropyran (49 g, 90%) as colorless viscous liquid: $^1$H-NMR (CDCl$_3$, 300 MHz,) δ 5.80-5.89 [m, 1H, =CH—C], 5.02-5.06 [m overlapping, 2H, =CH$_2$], 4.59-4.60 [m, 1H, 2-H of THP], 3.77-3.83 [m, 2H, —CH$_2$O], 3.44-3.50 [m, 2H, CH$_2$O of THP], 2.33-2.38 [m, 2H, CH$_2$—CH=CH$_2$], 1.51-1.71 [m, 6H, Hs of THP].

Into a 500-mL flask containing 2-(3-butenyloxy)tetrahydropyran (49.0 g, 0.314 mol) in CH$_2$Cl$_2$ (500 mL) under a nitrogen atmosphere and cooled to 0° C. was added freshly crystallized m-chloroperoxybenzoic acid (95 g, 0.55 mol). The mixture was maintained at 0° C. for a period of 24 h. The precipitated benzoic acid was removed via vacuum filtration. The filtrate thus obtained was washed successively with 10% aqueous sodium hydroxide (500 mL) and saturated aqueous sodium sulfite (500 mL), respectively, the organic layer dried over anhydrous MgSO$_4$ and concentrated in vacuo to afford tetrahydro-2-(oxiranylethoxy)-2H-pyran as a pure clear colorless liquid (52 g, 95%), which was used without any further purification: $^1$H NMR (CDCl$_3$, 300 MHz) δ 4.62 (s, 1H], 3.86-3.92 [m, 2H], 3.52-3.55 [m, 2H], 3.08 [br, 1H], 2.78-2.81 [t, J=3 Hz, 1H], 2.53-2.55 [t, J=3 Hz, 1H], 1.53-1.88 [m, 8H].

5-(3-Methoxyphenyl)-8,9-dimethyl-3-[(tetrahydro-2H-pyran-2-yl)oxy]methyl-2-oxa-8-azabicyclo[3.3.1]nonane (14). Into a dry 1 L flask containing a solution of 1,5-dimethyl-4-(3-methoxyphenyl)-1,2,3,6-tetrahydropyridine 7 (24 g, 0.11 mol) in dry THF (600 mL) cooled in a salted ice bath was added 1.4 M s-BuLi in cyclohexane (85 mL, 119 mmol) drop wise under a N$_2$ atmosphere over a period of 0.5 h. The dark red solution was further stirred at reduced temperature for an additional 15 min whereupon the mixture was cannula transferred into a second dry 2 L flask containing tetrahydro-2-(oxiranylethoxy)-2H-pyran (13) (20 g, 0.11 mol) in anhydrous Et$_2$O (150 mL) cooled to –10° C. Upon complete addition of the metalated enamine to the epoxide, the resulting mixture was stirred for additional 30 min at –5° C. The reaction was quenched with a solution of 13 g of NaOH and 42 g of NaCl in 350 mL H$_2$O at such a rate so as to maintain the solution temperature below 0° C. and the mixture subsequently poured into 500 mL H$_2$O. The layers were separated, and the aqueous layer extracted with Et$_2$O/EtOAc (1:1, 3×200 mL). The combined organic layers were dried over anhydrous K$_2$CO$_3$, concentrated, and purified via flash column chromatography on silica gel (50% EtOAc/hexanes to 100% EtOAc gradient) to afford 5-(3-methoxyphenyl)-8,9-dimethyl-3-[(tetrahydro-2H-pyran-2-yl)oxy]methyl-2-oxa-8-azabicyclo [3.3.1]nonane (14) as a mixture of diastereomers (30 g, 70%): LCMS (ESI): m/z 390.5 (M+H)$^+$; $^1$H NMR (CDCl$_3$, 300 MHz) δ 7.22-7.28 [m, 1H], 6.71-6.97 [m, 3H], 4.59 [br m, 1H], 4.48 [br m, 1H], 4.19 [br m, 1H], 3.81-3.87 [m, 2H], 3.80 [s, 3H], 3.52 [br m, 2H], 2.62-2.64 [m, 3H], 2.37 [s, 3H], 2.45 [m, 1H], 1.51-1.82 [m, 2H], 0.69 [d, J=6 Hz, 3H].

3-(2-Bromoethyl)-5-(methoxyphenyl)-8,9-dimethyl-2-oxa-8-azabicyclo[3.3.1]nonane (15). In a dry 1 L flask containing 5-(3-methoxyphenyl)-8,9-dimethyl-3-[(tetrahydro-2H-pyran-2-yl)oxy]methyl-2-oxa-8-azabicyclo[3.3.1] nonane 14 (30 g, 0.076 mol) and triphenylphospine (31 g, 0.12 mol) dissolved in anhydrous THF (600 mL) under a N$_2$ atmosphere and cooled to 0° C. was added Br$_2$ (6.0 mL, 117 mmol) over a period of 30 min. During the course of addition, the solution, which was initially clear yellowish, became precipitous slurry. Upon complete addition, the mixture was stirred 30 min at reduced temperature and overnight at room temperature (reaction mixture becomes homogenous brownish black). After this time MeOH (50 mL) was added drop wise and the mixture concentrated. The residue was partitioned between cold Et$_2$O (500 mL) and cold 1 N NaOH (500 mL). The organic layer was further washed with H$_2$O (400 mL), dried over anhydrous K$_2$CO$_3$ and concentrated to afford semisolid material. The residue obtained was redissolved in minimum amount of CHCl$_3$ and further diluted with hexane until precipitation of triphenylphosphine oxide was observed. Removal of precipitate followed by concentration of the filtrate and purification via flash chromatography (30% EtOAc/hexanes) afforded 20 g (70%) of 3-(2-bromoethyl)-5-(methoxyphenyl)-8,9-dimethyl-2-oxa-8-azabicyclo[3.3.1]nonane 15 as a mixture of diastereomers: LCMS (APCI): m/z 370.3 (M+H)$^+$; $^1$H NMR (CDCl$_3$, 300 MHz) δ 7.24-7.29 [m, 1H], 6.73-6.90 [m, 3H], 4.51-4.52 [m, 2H], 3.80 [s, 3H], 3.52-3.56 [m, 2H], 2.61-2.66 [m, 3H], 2.36 [s, 3H], 1.71-2.04 [m, 5H], 0.69 [d, J=6 Hz, 3H].

This material was used in the next step without further purification.

N,8a-Dimethylmethyl-4a-(3-methoxyphenyl)octahydro-6-isoquinolinol (17). A solution of 3-(2-bromoethyl)-5-(methoxyphenyl)-8,9-dimethyl-2-oxa-8-azabicyclo[3.3.1] nonane (15) (9.6 g, 0.026 mol), acetic anhydride (35 mL) and trifluoroacetic acid (35 mL) were stirred under N$_2$ atmosphere at ambient temperature for 1 h, poured into a mixture of ice (300 g) and 50% aqueous NaOH (50 mL) sufficient to make solution strongly basic and the product extracted into cold Et$_2$O (400 mL). The ether layer was washed once with cold H$_2$O, dried over anhydrous K$_2$CO$_3$ and concentrated at 0° C. to afford yellow viscous oil (10.8 g). The oil was directly taken up in molecular sieve dried CH$_3$CN (200 mL) and refluxed over K$_2$CO$_3$ (12 g) for 3 h under an N$_2$ atmosphere. Upon cooling, the solution was filtered, concentrated and the residue taken up in dry MeOH (200 mL). The solution was cooled to 0° C. whereupon NaBH$_4$ (11.9 g, 0.031 mol) was added over 30 min. The mixture was gradually warmed to room temperature and stirred for 36 h. The reaction was quenched with the addition of 4N aqueous HCl (pH 1) and stirred an additional 15 min whereupon the solution was made basic (pH 14) through the addition of cold 50% aqueous NaOH. The resulting solution was concentrated and partitioned between 1:1 mixture of Et$_2$O/EtOAc (200 mL) and H$_2$O (200 mL). The aqueous phase was further extracted with 1:1 mixture of Et$_2$O/EtOAc (2×100 mL) and the combined organic layers dried over anhydrous K$_2$CO$_3$/Na$_2$SO$_4$, concentrated to afford crude product (6.72 g). Purification via flash chromatography (35%. EtOAc/hexanes gradient) using neutral alumina (activity II-III) afforded a diastereomeric mixture of alcohol N,8a-dimethylmethyl-4a-(3-methoxyphenyl)octahydro-6-isoquinolinol (11) as almost colorless viscous oil (4.39 g, 58%): LCMS (APCI) 15: m/z 412.4 (M+H)$^+$; LCMS (APCI) 15: m/z 290.4 (M+H)$^+$; $^1$H-NMR (CDCl$_3$, 300 MHz) 11 δ 7.12-7.26 [m, 3H], 6.72-6.91 [m, 1H], 4.01 [m, 1H], 3.80 [s, 3H], 2.63-2.79 [m, 2H], 2.31 [s, 3H], 2.26-2.28 [m, 3H], 2.17-2.21 [m, 2H], 2.03-2.10 [m, 2H], 1.86 [m, 1H], 1.63-1.73 [m, 2H], 1.40 [m, 2H], 1.19 [s, 3H]; $^{13}$C NMR (CDCl$_3$, 300 MHz) 11 δ 158.8, 149.3, 128.2, 121.3, 116.0, 109.8, 67.5, 64.9, 55.1, 52.6, 46.7, 43.9, 41.4, 36.2, 35.7, 35.1, 30.9, 25.3.

This material was used in the next step without further purification.

N-Methyl-4a-(3-methoxyphenyl)octahydro-6-oxa-decahydroisoquinoline (18). Into a dry flask containing oxalyl chloride (3.45 mL, 6.9 mmol, 2.0 M solution in CH$_2$Cl$_2$) in CH$_2$Cl$_2$ (15 mL) cooled to –70° C. was added DMSO (0.83 mL, 11.7 mmol) in CH$_2$Cl$_2$ (10 mL) over 10 min. The solution was stirred for an additional 10 min at −70° C. and 1.54 g, 5.32 mmol of compound 17 in CH$_2$Cl$_2$ was added over 30 min. After an additional 30 min at −70° C., Et$_3$N (1.11 mL, 7.98 mmol) was added and the solution warmed to room temperature, washed with saturated aqueous NaHCO$_3$ (100 mL), dried over Na$_2$SO$_4$, concentrated and purified via flash chromatography (4% MeOH—CHCl$_3$) to afford 1.40 g (92%) of 18: LCMS (ESI): m/z 288.6 (M+H)$^+$; $^1$H NMR (CDCl$_3$, 300 MHz) δ 7.18 [t, J=3 Hz, 1H], 6.75-6.83 [m, 3H], 3.76 [s, 3H], 3.05 [d, J=15 Hz, 1H], 2.73-2.94 [m, 2H], 2.35-2.63 [m, 6H], 2.33 [s, 3H], 1.77 [m, 1H], 1.27-1.32 [m, 2H], 0.97 [s, 3H]; $^{13}$C NMR [CDCl$_3$, 300 MHz] δ 213.3, 159.3, 147.1, 128.8, 121.1, 115.1, 111.7, 63.1, 55.4, 52.6, 47.3, 47.1, 45.7, 37.8, 36.4, 33.8, 32.9, 25.8. This product was used in the next step without further purification.

2,8a-Dimethyl-4a-(3-methoxyphenyl)octahydroisoquinolin-6-one Oxime (19). N-Methyl-4aβ-(3-methoxyphenyl)octahydro-6-oxadecahydroisoquinoline 17 (1.41 g, 4.9 mmol) and hydroxylamine hydrochloride (1.70 g, 24.5 mmol) in EtOH (absolute, 100 mL) were heated to reflux for 5 h. The reaction mixture was allowed to cool to room temperature. Ethanol was removed under reduced pressure. The crude product was taken in to aqueous 2N NaOH solution (100 mL) and extracted with 3:1 CH$_2$Cl$_2$/THF (4×50 mL). The combined organic layers were dried (Na$_2$SO$_4$), filtered, and concentrated under reduced pressure yielding crude product. The crude product was purified by flash chromatography (neutral alumina, Brockmann activity II-III) eluting with 9:1 ethyl acetate/hexane to afford 1.43 g (96%) of 19 as a white solid (mixture of E/Z): LCMS (ESI): m/z 303.5 (M+H)$^+$.

N-Methyl-6-amino-4a-(3-methoxyphenyl)-8a-methyloctahydroisoquinoline (20). A slurry of oxime 19 (2.35 g, 0.077 mol) in anhydrous isopropanol (100 mL) and anhydrous toluene (200 mL) was heated to reflux until the solution became clear. The heat was turned off, and Na (20 g, 0.87 mol) was added carefully in a such rate that a steady reflux was maintained (make 30-40 pieces and store under hexane) over 1.5 h. The first addition was kept small. (Note hydrogen evolution!). At the end the reaction was slower, so the heating mantle was turned back on to speed things up. The reaction mixture was heated to reflux until all Na was consumed followed by cooling to 50° C. and quenching with careful addition of water (250 mL). The toluene layer was separated and the aqueous layer extracted with EtOAc (3×100 mL). The combined organic layers were dried (MgSO$_4$), filtered, and concentrated under reduced pressure yielding crude product. The crude product was purified by flash chromatography (50% CMA80 in CHCl$_3$) to afford 2.11 g (94%) of 20 as a colorless oil: LCMS (APCI): m/z 289.4 (M+H)$^+$; $^1$H NMR (CDCl$_3$, 300 MHz) δ 7.14-7.44 [m, 3H], 6.71-6.74 [m, 1H], 3.80 [s, 3H], 3.05 [m, 1H], 2.77 [m, 1H], 2.64 [d, J=12 Hz, 1H], 2.27-2.30 [m, 2H], 2.26 [s, 3H], 2.02-2.12 [m, 3H], 1.68-1.71 [m, 2H], 1.46-1.49 [m, 2H], 1.24 [m, 3H], 1.20 [s, 3H]; $^{13}$C NMR (CDCl$_3$, 300 MHz) δ 159.2, 150.2, 128.5, 121.8, 116.5, 110.0, 65.4, 55.5, 53.0, 47.1, 46.7, 43.8, 43.3, 36.6, 36.2, 32.2, 25.8.

The product was used in the next step without further purification.

N-Methyl-6-amino-4a-(3-methoxyphenyl)-8a-methyloctahydroisoquinoline Phthalimide (21). Amine 20 (1.70 g, 0.0058 mol) was dissolved in anhydrous toluene (100 mL) followed by the addition of phthalic anhydride (2.61 g, 0.018 mol), and the mixture was refluxed with Dean-Stark trap overnight. The solution was then cooled, washed with 1 N NaOH (3×50 mL) and water. The organic layer was collected, dried (Na$_2$SO$_4$) and the solvent removed under reduced pressure yielding crude product. The crude product was purified by flash chromatography (30% EtOAc/hexanes on neutral Al$_2$O$_3$ Brockman activity II-III) to afford 2.22 g (90%) of 21 as a white solid: LCMS (ESI): m/z 419.9 (M+H)$^+$; $^1$H NMR (CDCl$_3$, 300 MHz) δ 7.80-7.83 [m, 2H], 7.68-7.71 [m, 2H], 7.23-7.27 [m, 3H], 6.77-6.79 [m, 1H], 4.81 [m, 1H], 3.85 [s, 3H], 3.28 [t, J=12 Hz, 1H], 3.01 [d, J=12 Hz, 1H], 2.83-2.85 [m, 1H], 2.65-2.81 [m, 1H], 2.40-2.47 [m, 2H], 2.37 [s, 3H], 2.16-2.20 [m, 1H], 1.89 [ddd, J$_1$=J$_2$=15 Hz, J$_3$=6 Hz, 1H], 1.48-1.58 [m, 3H], 1.33-1.39 [m, 1H], 1.26 [s, 3H]; $^{13}$C NMR (CDCl$_3$, 300 MHz) δ 168.8, 159.2, 148.4, 134.1, 132.4, 128.7, 123.3, 121.8, 116.0, 111.0, 64.8, 55.5, 52.9, 47.8, 47.2, 43.8, 36.7, 35.6, 34.1, 26.7, 24.3.

Amino-4a-(3-methoxyphenyl)-8a-methyloctahydroisoquinoline Phthalimide (22). To a solution of 21 (2.09 g, 0.05 mol) in anhydrous 1,2-dichloroethane (100 mL) at reflux was added 1-chloroethyl chloroformate (0.82 mL, 7.47 mmol) drop wise. The resulting solution was heated under reflux for 5 h and then cooled to room temperature. This was then washed 1 time with saturated bicarbonate solution, 1× with water and then organic layer was evaporated and the resulting carbamate (foamy white solid, almost quantitative yield) was dissolved immediately in methanol (100 mL) and then refluxed overnight. After cooling to room temperature, methanol was removed under reduced pressure and the residue was treated with saturated sodium bicarbonate solution. This was then extracted with 3:1, CH$_2$Cl$_2$/THF, and the combined organic extracts were washed once with water. Removal of solvent under reduced pressure afforded 2.01 g (99%) of 22 as a white foamy solid: LCMS (APCI): m/z 405.2 (M+H)$^+$; $^1$H NMR (CDCl$_3$, 300 MHz) δ 7.80-7.83 [m, 2H], 7.68-7.71 [m, 2H], 7.23-7.28 [m, 3H], 6.78-6.81 [m, 1H], 4.84 [m, 1H], 3.86 [s, 1H], 3.75-3.80 [m, 2H], 3.32 [t, J=12 Hz, 1H], 3.03-3.15 [m, 2H], 2.90 [br s, 1H], 2.61-2.67 [m, 1H], 2.45 [d, J=12 Hz, 1H], 2.27-2.31 [m, 1H], 1.83-1.93 [m, 2H], 1.64 [dd, J$_1$=15 Hz, J$_2$=6 Hz, 2H], 1.31-1.48 [m, 3H], 1.24 [s, 3H]; $^{13}$C NMR (CDCl$_3$, 300 MHz) δ 167.5, 158.1, 147.0, 132.9, 131.1, 127.5, 122.1, 120.5, 114.7, 109.8, 67.0, 54.3, 53.2, 46.5, 43.5, 41.8, 35.2, 34.8, 33.9, 32.9, 29.4, 24.7, 24.1, 22.9.

The product was used in the next step without further purification.

N-(3-Phenylpropyl)-6-amino-4a-(3-methoxyphenyl)-8a-methyloctahydro-isoquinoline Phthalimide (23). Hydrocinnamaldehyde (0.65 mL, 0.0049 mol) and compound 22 (2.00 g, 0.0049 mol) were mixed in anhydrous 1,2-dichloroethane (50 mL) and then treated with sodium triacetoxyborohydride (1.57 g, 0.0074 mol). The reaction mixture remains cloudy throughout the reaction. The mixture was stirred at room temperature under N$_2$ atmosphere for 3 h. Reaction was monitored by TLC (20% EtOAc/hexanes; neutral Al$_2$O$_3$ Brockman activity II-III). After completion, the reaction mixture was quenched by adding saturated aqueous NaHCO$_3$, and the product was extracted with EtOAc (3×50 mL). The combined EtOAc extract were dried (MgSO$_4$), and the solvent was removed under reduced pressure to give crude product. The crude product was purified by flash chromatography (10% EtOAc/hexanes on neutral Al$_2$O$_3$ Brockman activity II-III) to afford 2.25 g (87%) of 23 as a white shiny solid. The sample used for X-ray analysis was recrystallized from a hexane and methylene chloride mixture: mp 136-138° C.; LCMS (ESI): m/z 523.7 (M+H)$^+$; $^1$H NMR (CDCl$_3$, 300 MHz) δ 7.79-7.82 [m, 2H], 7.68-7.71 [m, 2H], 7.18-7.32 [m, 8H], 6.76-6.81 [m, 1H], 4.81 [m, 1H], 3.85 [s, 3H], 3.31 [t, J=12 Hz, 1H], 2.94 [d, J=12 Hz, 1H], 2.80 [d, J=9 Hz, 1H], 2.67-2.73 [m, 1H], 2.34-2.53 [m, 4H], 2.25 [d, J=12 Hz, 1H], 1.78-1.94 [m, 3H], 1.51-1.62 [m, 2H], 1.49 [d, J=12 Hz, 1H], 1.31-1.37 [m, 1H], 1.26 [s, 3H]; $^{13}$C NMR (CDCl$_3$, 300 MHz) δ 170.4, 160.9, 150.3, 144.5, 135.7, 134.0, 130.4, 130.3, 130.2, 127.6, 124.9, 123.5, 117.6, 112.6, 90.0, 63.6, 59.9, 57.2, 52.9, 49.5, 46.2, 38.6, 38.5, 37.3, 35.7, 35.6, 31.0, 28.3, 25.9. Anal. (C$_{34}$H$_{38}$N$_2$O$_3$) C, H, N.

N-(3-Phenylpropyl)-6-amino-4a-(3-methoxyphenyl)-8a-methyloctahydroisoquinoline (24). Compound 23 (2.00 g, 0.0038 mol) and hydrazine hydrate (1.02 mL, 21.0 mmol) were dissolved in ethanol (100 mL) and refluxed overnight. The solution was then cooled, and the white precipitate was filtered and washed with cold ethanol. The solution was concentrated under reduced pressure and the crude material taken up in 3:1, CH$_2$Cl$_2$/THF (100 mL). The resulting white precipitate was filtered and washed with cold CH$_2$Cl$_2$ (50 mL). The combined organic layer was dried (Na$_2$SO$_4$) and concentrated under reduced pressure to yield crude product. The crude product was purified by flash chromatography (40% CMA 80 in CHCl$_3$) to afford 1.45 g (97%) of 24 as a colorless oil: LCMS (APCI): m/z 393.8 (M+H)$^+$; $^1$H NMR (CDCl$_3$, 300 MHz) δ 7.14-7.30 [m, 8H], 6.70-6.74 [m, 1H], 3.86 [s, 3H], 3.05 [m, 1H], 2.77-2.79 [br m, 1H], 2.65 [ddd, J$_1$=J$_2$=9 Hz, J$_3$=3 Hz, 2H], 2.58 [d, J=12 Hz, 1H], 2.26-2.36 [m, 4H], 2.04-2.12 [m, 3H], 1.68-1.81 [m, 4H], 1.44-1.50 [m, 4H], 1.32 [m, 1H], 1.21 [s, 3H]; $^{13}$C NMR (CDCl$_3$, 300 MHz) δ 159.2, 150.3, 142.9, 128.9, 128.6, 128.5, 126.0, 121.8, 116.5, 110.0, 62.6, 58.2, 55.5, 51.3, 46.9, 44.5, 43.2, 36.7, 36.3, 34.0, 32.1, 29.2, 25.8.

The product was used to synthesize acylamino analogues 6d-g without further purification.

N-(4a-(3-Methoxyphenyl)-8a-methyl-2-(3-phenylpropyl) octahydroisoquinolin-6-yl]-3-piperidin-1-yl-propionamide (25a). To compound 24 (105 mg, 0.267 mmol) dissolved in anhydrous THF (15 mL) was added 1-piperidinepropionic acid (63 mg, 0.40 mmol), triethylamine (0.17 mL, 1.33 mmol), and BOP reagent (140 mg, 0.32 mmol), and the reaction mixture was allowed to stir at room temperature for 1.5 h. Reaction progress was monitored by TLC (50% CMA 80 in CH$_2$Cl$_2$). The reaction mixture was diluted with EtOAc (25 mL) and washed with saturated aqueous NaHCO$_3$ (25 mL) followed by water (25 mL). The aqueous layers were back extracted with EtOAc (2×20 mL). The combined organic layers were washed with 1 N NaOH (25 mL), dried (MgSO$_4$), and concentrated under reduced pressure to afford crude amide. The crude product was purified by flash chromatography (30% CMA 80 in CH$_2$Cl$_2$) to afford 121 mg (85%) of 25a as a shiny white solid: LCMS (ESI): m/z 532.8 (M+H)$^+$; $^1$H NMR (CDCl$_3$, 300 MHz) δ 8.77 [d, J=6 Hz, 1H], 7.15-7.30 [m, 8H], 6.72-6.75 [m, 1H], 4.24 [m, 1H], 3.82 [s, 3H], 2.76 [br, 1H], 2.65-2.68 [m, 2H], 2.42-2.56 [m, 3H], 2.32-2.37 [m, 6H], 2.07-2.30 [m, 7H], 1.62-1.83 [m, 5H], 1.59-1.61 [m, 4H], 1.48-1.59 [m, 4H], 1.25-1.27 [br, 1H], 1.21 [s, 3H]; $^{13}$C NMR (CDCl$_3$, 300 MHz) δ 172.2, 159.2, 148.8, 142.8, 128.8, 128.7, 128.6, 126.0, 122.2, 116.2, 110.9, 62.4, 58.4, 55.6, 54.9, 54.0, 51.4, 45.5, 44.1, 38.1, 37.0, 36.8, 35.5, 34.0, 32.5, 29.2, 28.4, 26.9, 26.7, 24.6.

N-(4a-(3-Hydroxyphenyl)-8a-methyl-2-(3-phenylpropyl) octahydroisoquinolin-6-yl]-3-piperidin-1-yl-propionamide (6d) Dihydrochloride. To compound 25a (90 mg, 0.169 mmol), dissolved in anhydrous CH$_2$Cl$_2$ (15 mL) and cooled to −78° C., was added a 1.0 M solution in CH$_2$Cl$_2$ of BBr$_3$ (0.85 mL, 0.85 mmol) slowly. The reaction mixture was allowed to stir at −78° C. for 30 min and at RT for 2 h. The reaction was cooled to 0° C., quenched with saturated aqueous NaHCO$_3$ and extracted with CH$_2$Cl$_2$ (2×25 mL). The combined layers were washed with 1 N NaOH (25 mL), dried (Na$_2$SO$_4$), filtered and concentrated in vacuo to afford crude product. The crude product was purified by flash chromatography (40% CMA 80 in CH$_2$Cl$_2$) to afford 75 mg (86%) of 6d as a white solid: LCMS (ESI): m/z 518.9 (M+H)$^+$; $^1$H NMR (CDCl$_3$, 300 MHz) δ 8.73 [d, J=6 Hz, 1H], 7.09-7.31 [m, 8H], 6.68-6.72 [m, 1H], 4.30 [m, 1H], 2.78-2.85 [br, 1H], 2.59-2.69 [m, 4H], 2.50-2.55 [br, 4H], 2.36-2.42 [m, 4H], 2.20-2.27 [m, 3H], 2.05 [m, 2H], 1.78-1.85 [m, 5H], 1.62-1.65 [m, 4H], 1.43-1.50 [m, 4H], 1.21-1.25 [m, 2H], 1.19 [s, 3H]; $^{13}$C NMR (CDCl$_3$, 300 MHz) δ 171.8, 155.7, 148.2, 142.4, 128.5, 128.2; 125.7, 121.1, 116.5, 112.8, 61.8, 58.0, 54.3, 53.5, 50.9, 45.4, 43.6, 37.4, 36.6, 36.3, 35.0, 33.6, 31.9, 28.6, 27.9, 26.6, 25.9, 24.0.

An analytical sample, dihydrochloide salt, was prepared by dissolving the free base in MeOH and adding 6 equivalent of 1.0 M HCl in diethyl ether. Removal of solvent under reduced pressure afforded dihydrochloride salt as a white solid which was then crystallized from MeOH-Et$_2$O combination: mp 240-242° C. (fus.). Anal. (C$_{33}$H$_{49}$Cl$_2$N$_3$O$_2$.2.75H$_2$O) C, H, N.

3-(3,4-Dihydro-1H-isoquinolin-2-yl)-N-(4a-(3-methoxyphenyl)-8a-methyl-2-(3-phenylpropyl)octahydroisoquinolin-6-yl]propionamide (25b). To compound 24 (80 mg, 0.203 mmol) dissolved in anhydrous THF (15 mL) 3-(3,4-dihydro-1H-isoquinolin-2-yl)-propioinic acid hydrochloride (73 mg, 0.305 mmol), and triethylamine (0.142 mL, 1.01 mmol) was added, and the reaction mixture was stirred at room temperature for 15 min. After this time BOP reagent (99 mg, 0.22 mmol) was added, and the reaction mixture was allowed to stir at room temperature for 1.5 h. Reaction progress was monitored by TLC (50% CMA 80 in CH$_2$Cl$_2$). The reaction mixture was diluted with EtOAc (25 mL) and washed with saturated aqueous NaHCO$_3$ (25 mL) followed by water (25 mL). The aqueous layers were back extracted with EtOAc (2×20 mL). The combined organic layer was washed with 1 N NaOH (30 mL), dried (MgSO$_4$), and concentrated under reduced pressure to afford crude amide. The crude product was purified by flash chromatography (30% CMA 80 in CH$_2$Cl$_2$) to afford 94 mg (80%) of 25b as a shiny white solid: LCMS (ESI): m/z 580.9 (M+H)$^+$; $^1$H NMR (CDCl$_3$, 300 MHz) δ 8.29 [d, J=6 Hz, 1H], 7.03-7.31 [m, 12H], 6.70-6.73 m, 1H], 4.23 [m, 1H], 3.80 [s, 1H], 3.68 [s, 2H], 2.94 [t, J=6 Hz, 2H], 2.77-2.82 [m, 4H], 2.62-2.67 [m, 3H], 2.42 [t, J=6 Hz, 2H], 2.25-2.35 [m, 2H], 1.74-1.87 [m, 7H], 1.19-1.34 [m, 3H], 1.14 [s, 3H]; $^{13}$C NMR (CDCl$_3$, 300 MHz) δ 171.9, 159.2, 148.8, 142.8, 134.4, 134.1, 129.1, 128.9, 128.7, 128.6, 127.4, 126.9, 126.8, 126.3, 126.1, 122.1, 116.2, 110.8, 62.1, 58.2, 55.6, 54.1, 51.1, 50.5, 45.6, 44.0, 37.9, 36.8, 36.7, 35.3, 34.0, 33.0, 29.7, 29.2, 28.3, 26.8.

3-(3,4-Dihydro-1H-isoquinolin-2-yl)-N-(4a-(3-hydroxyphenyl)-8a-methyl-2-(3-phenylpropyl)octahydroisoquinolin-6-yl]propionamide (6e) Dihydrochloride. Compound 25b (70 mg, 0.120 mmol) was dissolved in anhydrous CH$_2$Cl$_2$ (15 mL), cooled to −78° C., and added to a 1.0 M solution of BBr$_3$ (0.60 mL, 0.60 mmol) in CH$_2$Cl$_2$ slowly. The reaction mixture was allowed to stir at −78° C. for 30 min and at RT for 1.5 h. The reaction was cooled to 0° C., quenched with saturated aqueous NaHCO$_3$ and extracted with CH$_2$Cl$_2$ (2×25 mL). The combined organic layer was dried (Na$_2$SO$_4$), filtered and concentrated in vacuo to afford crude product. The crude product was purified by flash chromatography (30% CMA 80 in CH$_2$Cl$_2$) to afford 60 mg (88%) of 63 as a white solid: LCMS (ESI): m/z 566.5 (M+H)$^+$; $^1$H NMR (CDCl$_3$, 300 MHz) δ 8.55 [d, J=6 Hz, 1H], 7.05-7.31 [m, 12H], 6.66-6.69 [m, 1H], 4.28 [m, 1H], 3.68 [s, 2H], 2.94 [t, J=6 Hz, 2H], 2.78-2.83 [m, 4H], 2.61-2.66 [3H], 2.45 [t, J=6 Hz, 2H], 2.23-2.34 [m, 3H], 2.02-2.13 [m, 2H], 1.69-1.80 [m, 8H], 1.25-1.32 [m, 3H], 1.11 [s, 3H]; $^{13}$CNMR (CDCl$_3$, 300 MHz) δ 172.2, 156.0, 148.6, 142.8, 134.3, 134.1, 129.1, 128.9, 126.6, 126.9, 126.3, 126.1, 111.1, 116.8, 113.2, 62.1, 58.2, 55.6, 54.0, 51.0, 50.4, 45.7, 43.9, 37.7, 36.8, 36.6, 35.2, 34.0, 32.8, 29.6, 29.1, 28.2, 27.0.

An analytical sample, dihydrochloide salt, was prepared by dissolving the free base in MeOH and adding 6 equivalent of 1.0 M HCl in diethyl ether. Removal of solvent under reduced pressure afforded dihydrochloride salt as a white solid which was then crystallized from a MeOH-EtOAc combination: mp 178-180° C. (fus.). Anal. ($C_{37}H_{49}Cl_2N_3O_2.2H_2O$) C, H, N.

1-Phenylcyclopentanecarboxylic Acid [4a-(3-Methoxyphenyl)-8a-methyl-2-(3-phenylpropyl)octahydroisoquinolin-6-yl]amide (25c). To compound 24 (71 mg, 0.180 mmol) dissolved in anhydrous THF (15 mL) was added 1-phenyl-1-cyclopentanecarboxylic acid (51 mg, 0.27 mmol), triethylamine (0.126 mL, 0.904 mmol), and BOP reagent (88 mg, 0.20 mmol), and the reaction mixture was allowed to stir at room temperature for 2 h. Reaction progress was monitored by TLC (30% CMA 80 in $CH_2Cl_2$). The reaction mixture was diluted with EtOAc (25 mL) and washed with saturated aqueous $NaHCO_3$ (25 mL) followed by water (25 mL). The aqueous layers were back extracted with EtOAc (2×20 mL). The combined organic layers were washed with 1 N NaOH (30 mL), dried ($MgSO_4$), and concentrated under reduced pressure to afford crude product. The crude product was purified by flash chromatography (25% CMA 80 in $CH_2Cl_2$) to afford 94 mg (92%): LCMS (ESI): m/z 565.6 (M+H)$^+$; $^1$H NMR ($CDCl_3$, 300 MHz) δ 7.17-7.36 [m, 13H], 6.71-6.73 [m, 1H], 4.92, [d, J=6 Hz, 1H], 4.19 [m, 1H], 3.79 [s, 3H], 2.74 [br, 1H], 2.62-2.64 [m, 2H], 2.33-2.45 [m, 5H], 2.10-2.31 [m, 2H], 1.98-2.09 [m, 3H], 1.61-1.84 [m, 10H], 1.46 [d, J=12 Hz, 1H], 1.20-1.33 [m, 2H], 1.15 [s, 3H]; $^{13}$C NMR ($CDCl_3$, 300 MHz) δ 176.1, 159.2, 148.9, 144.8, 142.8, 129.0, 128.9, 128.7, 128.6, 127.2, 127.1, 126.0, 121.9, 116.3, 110.7, 62.2, 59.6, 58.2, 55.5, 51.2, 46.2, 44.2, 37.8, 37.4, 37.2, 36.9, 36.6, 35.6, 33.9, 29.2, 28.1, 26.6, 24.4.

1-Phenylcyclopentanecarboxylic Acid [4a-(3-Hydroxyphenyl)-8a-methyl-2-(3-phenylpropyl)octahydroisoquinolin-6-yl]amide (6f) Hydrochloride. Compound 25c (94 mg, 0.166 mmol) was dissolved in anhydrous $CH_2Cl_2$ (15 mL), cooled to −78° C., and added to 1.0 M solution of $BBr_3$ (0.832 mL, 0.832 mmol) in $CH_2Cl_2$ slowly. The reaction mixture was allowed to stir at −78° C. for 30 min and at RT for 1.5 h. The reaction was cooled to 0° C., quenched with saturated aqueous $NaHCO_3$ and extracted with $CH_2Cl_2$ (2×25 mL). The combined organic layer was dried ($Na_2SO_4$), filtered, and concentrated in vacuo to afford crude product. The crude product was purified by flash chromatography (30% CMA 80 in $CH_2Cl_2$) to afford 78 mg (86%) of 6f as a white solid: LCMS (APCI): m/z 551.2 (M+H)$^+$; $^1$H NMR ($CDCl_3$, 300 MHz) δ 7.09-7.34 [m, 14H], 6.68-6.70 [br, 1H], 5.06 [d, J=9 Hz, 1H], 4.26 [m, 1H], 2.71 [br, 1H], 2.61-2.64 [m, 2H], 2.35-2.45 [m, 5H], 2.00-2.10 [m, 5H], 1.63-1.98 [m, 10H], 1.41 [d, J=12 Hz, 1H], 1.18-1.23 [m, 2H], 1.13 [s, 3H]; $^{13}$C NMR ($CDCl_3$, 300 MHz) δ 176.7, 156.2, 148.5, 144.5, 142.7, 129.1, 128.9, 128.7, 128.6, 127.3, 127.2, 126.0, 121.3, 116.8, 113.3, 62.1, 59.6, 58.2, 51.1, 46.4, 44.0, 37.5, 37.4, 37.3, 36.9, 36.6, 35.4, 33.9, 29.0, 28.0, 26.8, 24.4.

An analytical sample, hydrochloride salt, was prepared by dissolving the free base in MeOH and adding 3 equivalent of 1.0 M HCl in diethyl ether. Removal of solvent under reduced pressure afforded hydrochloride salt as a white solid which was then crystallized from a MeOH-EtOAc combination: mp 194-195° C. (fus.). Anal. ($C_{37}H_{47}ClN_3O_2.0.75H_2O$) C, H, N.

Benzo[b]thiophene-2-carboxylic Acid [4a-(3-Methoxyphenyl)-8a-methyl-2-(3-phenylpropyl)octahydroisoquinolin-6-yl]amide (25d). To compound 24 (52 mg, 0.132 mmol) dissolved in anhydrous THF (10 mL) was added benzo[b]thiophene-2-carboxylic acid (35 mg, 0.198 mmol), triethylamine (0.092 mL, 0.662 mmol), and BOP reagent (64 mg, 0.145 mmol), and the reaction mixture was allowed to stir at room temperature for 1.5 h. Reaction was monitored by TLC (30% CMA 80 in $CH_2Cl_2$). The reaction mixture was diluted with EtOAc (20 mL) and washed with saturated aqueous $NaHCO_3$ (20 mL) followed by water (20 mL). The aqueous layers were back extracted with EtOAc (2×20 mL). The combined organic layers were washed with 1 N NaOH (25 mL), dried ($MgSO_4$), and concentrated under reduced pressure to afford crude product. The crude product was purified by flash chromatography (20% CMA 80 in $CH_2Cl_2$) to afford 70 mg (96%): LCMS (ESI): m/z 553.9 (M+H)$^+$; $^1$H NMR ($CDCl_3$, 300 MHz) δ 7.74-7.81 [m, 3H], 7.36-7.40 [m, 2H], 7.18-7.31 [m, 7H], 6.74-6.75 [m, 1H], 6.12 [d, J=9 Hz, 1H], 4.47 [m, 1H], 3.81 [s, 3H], 2.76-2.79 [br, 1H], 2.59-2.67 [m, 3H], 2.36-2.39, [m, 2H], 2.15-2.29 [m, 4H], 1.89-1.94 [m, 3H], 1.60-1.81 [m, 4H], 1.53 [d, J=12 Hz, 1H], 1.26-1.32 [m 1H], 1.24 [s, 3H]; $^{13}$C NMR ($CDCl_3$, 300 MHz) δ 161.9, 159.3, 148.7, 142.8, 141.2, 139.5, 139.2, 128.9, 128.8, 128.7, 126.6, 126.1, 125.3, 125.2, 123.1, 122.0, 116.4, 110.8, 62.3, 58.3, 55.6, 51.2, 47.1, 44.4, 38.1, 37.0, 36.8, 35.6, 34.0, 29.2, 28.3, 26.7.

Benzo[b]thiophene-2-carboxylic Acid-4a-(3-hydroxyphenyl)-8a-methyl-2-(3-phenylpropyl)octahydroisoquinolin-6-yl]-amide (6g) Hydrochloride. Compound 25d (70 mg, 0.260 mmol) was dissolved in anhydrous $CH_2Cl_2$ (15 mL), cooled to −78° C., and added to 1.0 M solution of $BBr_3$ (0.633 mL, 0.633 mmol) in $CH_2Cl_2$ slowly. The reaction mixture was allowed to stir at −78° C. for 30 min and at RT for 1.5 h. The reaction was cooled to 0° C., quenched with saturated aqueous $NaHCO_3$, and extracted with $CH_2Cl_2$ (2×25 mL). The combined organic layer was dried ($Na_2SO_4$), filtered and concentrated in vacuo to afford crude product. The crude product was purified by flash chromatography (25% CMA 80 in $CH_2Cl_2$) to afford 60 mg (88%) of 6g as a white solid: LCMS (APCI): m/z 539.3 (M+H); $^1$H NMR ($CDCl_3$, 300 MHz) δ 7.77-7.81 [m, 3H], 7.37-7.41 [m, 2H], 7.25-7.27 [m, 3H], 7.12-7.19 [m, 5H], 6.73-6.76 [m, 1H], 6.27 [d, J=12 Hz, 1H], 4.48 [m, 1H], 2.74 [m, 1H], 2.58-2.65 [m, 3H], 2.36-2.38 [m, 2H], 2.15-2.26 [m, 4H], 1.78-1.86 [m, 5H], 1.56-1.70 [m, 1H], 1.47 [d, J=12 Hz, 1H], 1.21-1.23 [m, 2H], 1.19 [s, 3H]; $^{13}$C NMR ($CDCl_3$, 300 MHz) δ 162.0, 155.8, 148.2, 142.4, 140.9, 139.2, 138.6, 128.6, 128.4, 126.4, 125.8, 125.3, 125.1, 125.0, 122.8, 121.3, 116.5, 113.2, 61.9, 58.0, 50.8, 47.0, 43.9, 37.5, 36.7, 36.4, 35.2, 33.6, 28.7, 27.9, 26.4.

An analytical sample, hydrochloride salt, was prepared by dissolving the free base in MeOH and adding 3 equivalent of 1.0 M HCl in diethyl ether. Removal of solvent under reduced pressure afforded hydrochloride salt as a white solid which was then crystallized from a MeOH/EtOAc combination: mp 206-208° C. (fus.). Anal. ($C_{34}H_{39}Cl_2N_2O_2S.0.75H_2O$) C, H, N.

Biological Activity

Determination of apparent affinity ($K_e$). The ability of a single concentration of test compound to shift an agonist dose response curve to the right was used to determine its $K_e$. Agonist activity was determined using [$^{35}$S]GTP-γ-S binding in CHO cell membrane homogenates expressing either the human mu, kappa or delta opioid receptor. The subtype selective agonists (D-Ala$^2$, MePhe$^4$, Gly-ol$^5$)enkephalin (DAMGO, mu receptor), D-Pen2,D-Pen5]-enkephalin (DP-DPE, delta receptor) or U69,593 (kappa receptor) were run as appropriate. The assays were run in triplicate in 1.4 mL polypropylene tubes (Matrix Technologies, Hudson, N.H.) in 96-well format. Each assay tube contained membrane homogenate, one of seven concentrations of agonist or agonist+test compound, 0.1 nM [$^{35}$S]GTP-γ-S and 10 μM GDP in a 50 mM HEPES buffer (pH 7.4). Basal [$^{35}$S]GTP-γ-S binding was determined in samples without agonist or test compound. All samples were incubated at room temperature for one hour after which bound radioligand was separated from free via rapid vacuum filtration over GF-B filters with a Brandel Scientific (Gaithersburg, Md.) 96-well harvester. Bound radioactivity was determined with a TopCount 12-detector instrument (Packard Instruments) using standard scintillation counting techniques. The binding data from each assay plate were normalized to basal binding prior to analysis. The $EC_{50}$s were calculated from a three-parameter logistic curve fit to the data with Prism (version 3.0, GraphPad Software, Inc., San Diego, Calif.). The $EC_{50}$ values for Agonist (A) and agonist+test compound (A') were used to calculate the test compound $K_e$ from the formula: $K_e$=[L]/(DR−1), where [L] equals the concentration of test compound in the assay and DR equals the dose ratio or A'/A. The A' was used only when it was at least 2-fold greater than A.

TABLE 1

Inhibition of Agonist Stimulated [$^{35}$S]GTPγS Binding by Compounds in Cloned Human μ, δ, and κ Opioid Receptors

| RTI-5989 | compd | μ, DAMGO $K_e$ (nM) | δ, DPDPE $K_e$ (nM) | κ, U69,593 $K_e$ (nM) | μ/κ | δ/κ |
|---|---|---|---|---|---|---|
| 90 | 6a | 99.4 ± 28.3 | 477 ± 137 | 3.37 ± 0.47 | 29 | 141 |
| 91 | 6b | 0.84 ± 0.22 | 18.9 ± 5.2 | 2.84 ± 0.97 | 0.3 | 7 |
| 92 | 6c | 0.80 ± 0.10 | 12.4 ± 2.9 | 1.03 ± 0.14 | 0.8 | 12 |
| 170 | 6d | 41.7 ± 7.8 | 12.3 ± 3.1 | 0.27 ± 0.08 | 154 | 46 |
| 175 | 6e | 9.82 ± 3.7 | 4.56 ± 1.2 | 0.22 ± 0.02 | 45 | 21 |
| 176 | 6f | 1.46 ± 0.15 | 6.46 ± 2.3 | 1.93 ± 0.48 | 0.8 | 3 |
| 177 | 6g | 11.3 ± 2.0 | 1.01 ± 0.22 | 0.46 ± 0.13 | 25 | 2 |
| | JDTic | 3.41 | 79.3 | 0.01 | 341 | 7930 |
| | nor-BNI | 19 | 4.4 | 0.04 | 475 | 110 |
| | naltrexone | 3.35 ± 0.95 | 60.7 ± 10.6 | 4.63 ± 1.49 | | |
| | LY255,582 | 0.10 ± 0.04 | 0.60 ± 0.11 | 0.29 ± 0.06 | | |

[a]The data represent the mean ± SE from at least three independent experiments. The final GDP assay concentration was 10 μM.

REFERENCES (1) Aldrich, J. V. Narcotic Analgesics. In *Burger's Medicinal Chemistry and Drug Discovery*, 6th ed.; Abraham, D. J. Ed.; John Wiley & Sons: New York, 2003; Vol. 6, Chapter 7.

(2) Kreek, M. J.; LaForge, K. S.; Butelman, E. Pharmacotherapy of addictions. *Nat. Rev. Drug Discov.* 2002, 1, 710-726.

(3) Jones, R. M.; Hjorth, S. A.; Schwartz, T. W.; Portoghese, P. S. Mutational evidence for a common kappa antagonist binding pocket in the wild-type kappa and mutant mu[K303E] opioid receptors. *J. Med. Chem.* 1998, 41, 4911-4914.

(4) Jones, R. M.; Portoghese, P. S. 5'-Guanidinonaltrindole, a highly selective and potent kappa-opioid receptor antagonist. *Eur. J. Pharmacol.* 2000, 396, 49-52.

(5) Portoghese, P. S.; Lipkowski, A. W.; Takemori, A. E. Binaltorphimine and nor-binaltorphimine, potent and selective κ-opioid receptor antagonists. *Life Sci.* 1987, 40, 1287-1292.

(6) Stevens, W. C., Jr.; Jones, R. M.; Subramanian, G.; Metzger, T. G.; Ferguson, D. M.; Portoghese, P. S. Potent and selective indolomorphinan antagonists of the kappa-opioid receptor. *J. Med. Chem.* 2000, 43, 2759-2769.

(7) Thomas, J. B.; Mascarella, S. W.; Rothman, R. B.; Partilla, J. S.; Xu, H.; McCullough, K. B.; Dersch, C. M.; Cantrell, B. E.; Zimmerman, D. M.; Carroll, F. I. Investigation of the N-substituent conformation governing potency and μ receptor subtype-selectivity in (+)-(3R,4R)-dimethyl-4-(3-hydroxyphenyl)piperidine opioid antagonists. *J. Med. Chem.* 1998, 41, 1980-1990.

(8) Thomas, J. B.; Fall, M. J.; Cooper, J. B.; Rothman, R. B.; Mascarella, S. W.; Xu, H.; Partilla, J. S.; Dersch, C. M.; McCullough, K. B.; Cantrell, B. E.; Zimmerman, D. M.; Carroll, F. I. Identification of an opioid κ receptor subtype-selective N-substituent for (+)-(3R,4R)-dimethyl-4-(3-hydroxyphenyl)piperidine. *J. Med. Chem.* 1998, 41, 5188-5197.

(9) Thomas, J. B.; Atkinson, R. N.; Vinson, N. A.; Catanzaro, J. L.; Perretta, C. L.; Fix, S. E.; Mascarella, S. W.; Rothman, R. B.; Xu, H.; Dersch, C. M.; Cantrell, B. E.; Zimmerman, D. M.; Carroll, F. I. Identification of (3R)-7-hydroxy-N-((1S)-1-[[(3R,4R)-4-(3-hydroxyphenyl)-3,4-dimethyl-1-piperidinyl]methyl]-2-methylpropyl)-1,2,3,4-tetrahydro-3-isoquinolinecarboxamide as a novel potent and selective opioid kappa receptor antagonist. *J. Med. Chem.* 2003, 46, 3127-3137.

(10) Thomas, J. B.; Atkinson, R. N.; Rothman, R. B.; Fix, S. E.; Mascarella, S. W.; Vinson, N. A.; Xu, H.; Dersch, C. M.; Lu, Y.; Cantrell, B. E.; Zimmerman, D. M.; Carroll, F. I. Identification of the first trans-(3R,4R)-dimethyl-4-(3-hydroxyphenyl)piperidine derivative to possess highly potent and selective opioid kappa receptor antagonist activity. *J. Med. Chem.* 2001, 44, 2687-2690.

(11) Carroll, F. I.; Thomas, J. B.; Dykstra, L. A.; Granger, A. L.; Allen, R. M.; Howard, J. L.; Pollard, G. T.; Aceto, M. D.; Harris, L. S. Pharmacological properties of JDTic: A novel κ-opioid receptor antagonist. *Eur. J. Pharmacol.* 2004, 501, 111-119.

(12) Thomas, J. B.; Zheng, X.; Mascarella, S. W.; Rothman, Richard B.; Dersch, Christina M.; Partilla, John S.; Flippen-Anderson, Judith L.; George, Clifford F.; Cantrell, B. E.; Zimmerman, Dennis M.; Carroll, F. I. N-Substituted 9β-methyl-5-(3-hydroxyphenyl)morphans are opioid receptor pure antagonists. *J. Med. Chem.* 1998, 41, 4143-4149.

(13) Zimmerman, D. M.; Nickander, R.; Horng, J. S.; Wong, D. T. New structural concepts for narcotic antagonists defined in a 4-phenylpiperidine series. *Nature* 1978, 275, 332-334.

(14) Zimmerman, D. M.; Leander, J. D.; Cantrell, B. E.; Reel, J. K.; Snoddy, J.; Mendelsohn, L. G.; Johnson, B. G.; Mitch, C. H. Structure-activity relationships of the trans-3,4-dimethyl-4-(3-hydroxyphenyl)piperidine antagonists for μ and κ opioid receptors. *J. Med. Chem.* 1993, 36, 2833-2841.

The invention claimed is:

1. A compound represented by the formula:

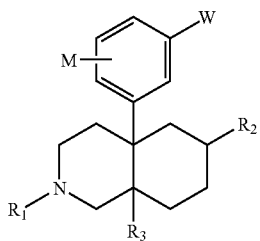

wherein

M is hydrogen, halogen, $C_1$-$C_4$ alkyl, CN, $OC_{1-8}$ alkyl, $OC_{3-8}$ alkenyl, $OC_{3-8}$ alkynyl, or $OC_{1-8}$ alkylaryl;

$R_1$ is $C_{1-8}$ alkyl, $C_{3-8}$ alkenyl, $C_{3-8}$ alkynyl, $C_{1-8}$ alkylaryl,

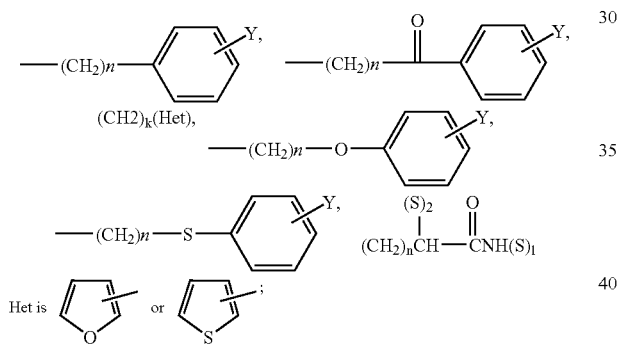

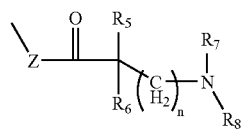

$(S)_1$ is hydrogen, $CH_2CO_2H$, $CH_2CO_2CH_3$, or $CH_2CO_2C_2H_5$;

$(S)_2$ is hydrogen, $CH_3$, $C_2H_3$, $CH_2C_6H_5$, or $CH_2CH_2C_6H_5$;

$R_2$ is =O, hydrogen, $NR_7R_8$,

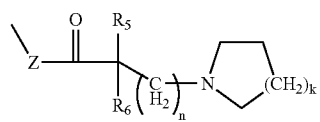
(a)

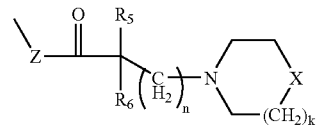
(b)

(c)

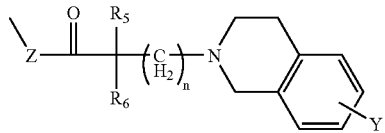
(d)

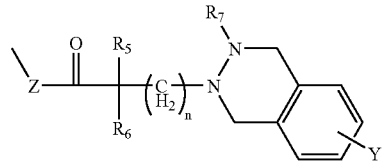
(e)

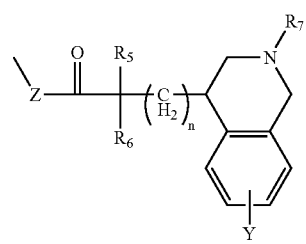
(f)

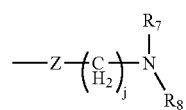
(g)

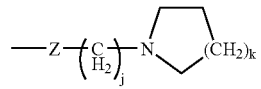
(h)

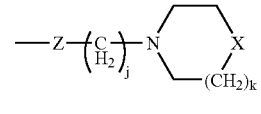
(i)

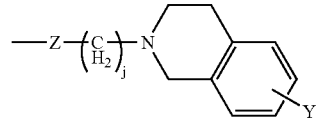
(j)

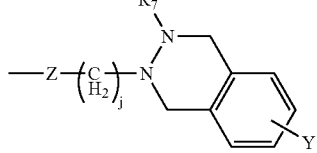
(k)

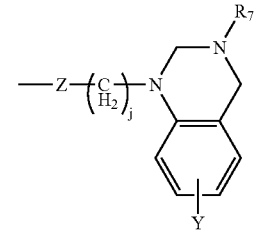
(l)

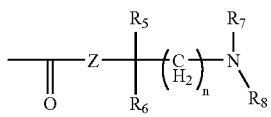
(m)

-continued
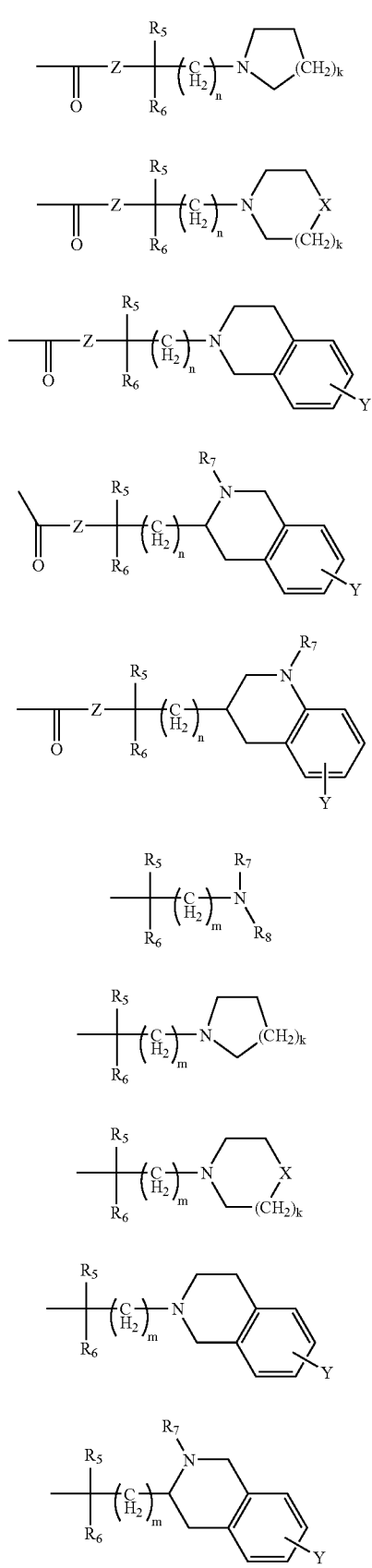
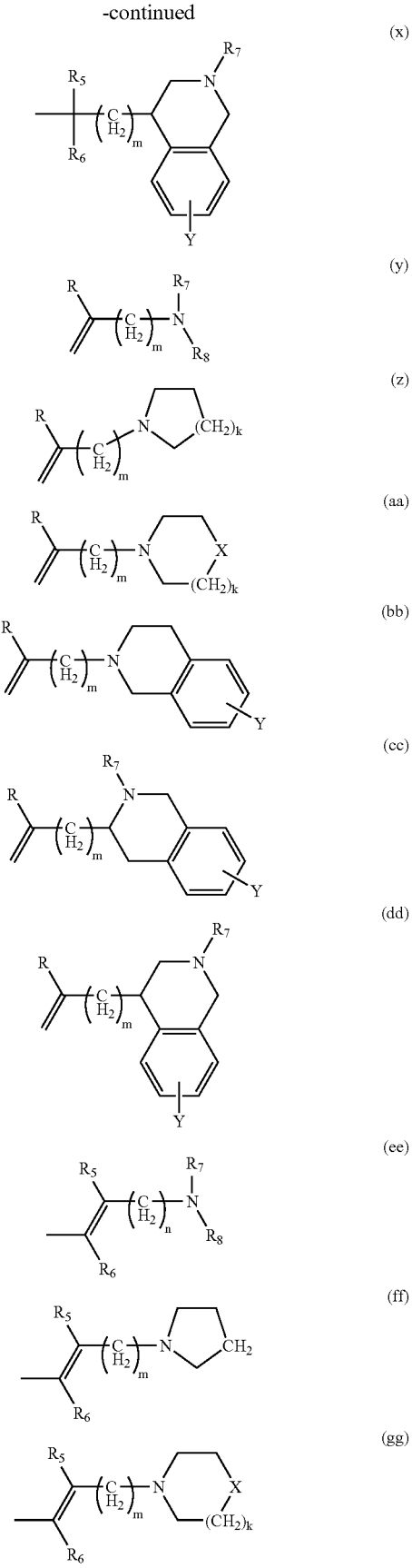

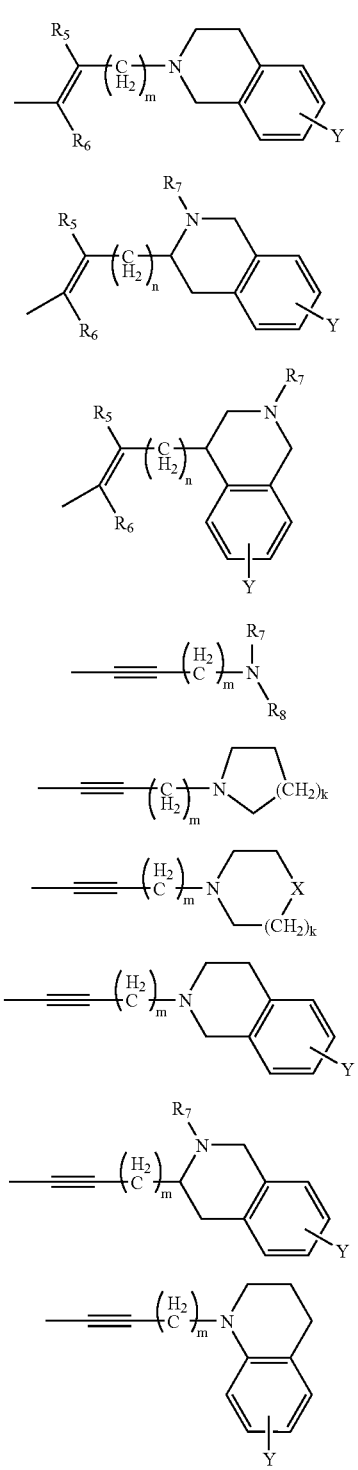

X is NR, O, or S;
Y is OH, OR$_9$, C$_{1-8}$ alkyl, F, Cl, Br, CF$_3$, or CN;
R is hydrogen, C$_{1-8}$ alkyl, C$_{3-8}$ alkenyl, C$_{3-8}$ alkynyl, C$_{1-8}$ alkylaryl, or CO$_2$R$_9$;
W is hydrogen, OH, OCOR$_9$, N(R$_4$)$_2$, NR$_3$COR$_9$, NR$_3$SO$_2$R$_9$, NR$_3$CO$_2$R$_9$, CONH$_2$, or NHCHO;
Z is NR3, O, or S;
n is 1, 2, or 3;

m is 1, 2, 3, or 4;
j is 2, 3, or 4;
k is 1 or 2;
each R$_3$ is, independently, C$_{1-3}$ alkyl, C$_{3-8}$ alkenyl, C$_{3-8}$ alkynyl, C$_{1-8}$ alkylaryl, CH$_2$Y, or CO$_2$R;
each R$_4$ is, independently, hydrogen, C$_{1-8}$ alkyl, C$_{3-8}$ alkenyl, C$_{3-8}$ alkynyl, or C$_{1-8}$ alkylaryl;
R$_5$ and R$_6$ are each, independently, hydrogen, C$_{1-8}$ alkyl, C$_{3-8}$ alkenyl, C$_{3-8}$ alkynyl, C$_{1-8}$ alkylcycloalkyl, or C$_{1-8}$ alkylaryl;
R$_7$ and R$_8$ are each, independently, hydrogen, C$_{1-8}$ alkyl, C$_{3-8}$ alkenyl, C$_{3-8}$ alkynyl, C$_{1-8}$ alkylcycloalkyl, or C$_{1-8}$ alkylaryl,
R$_9$ is C$_{1-8}$ alkyl, C$_{3-8}$ alkenyl, C$_{3-8}$ alkynyl, or C$_{1-8}$ alkylaryl,
or a pharmaceutically acceptable salt thereof and inclusive of stereoisomers and
wherein the compound may be isotopically labeled.

2. The compound of claim 1, which is represented by the formula:

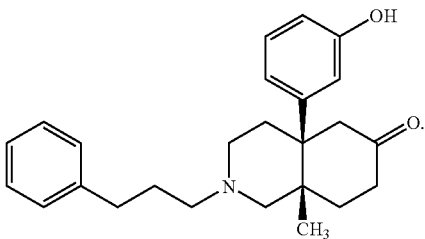

3. The compound of claim 1, which is represented by the formula:

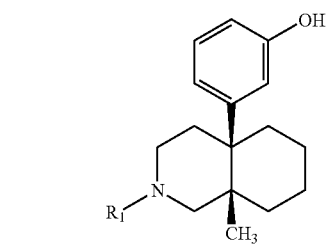

wherein R is CH$_3$, C$_6$H$_5$(CH$_2$)$_2$ or C$_6$H$_5$(CH$_2$)$_3$.

4. The compound of claim 1, which is represented by the formula:

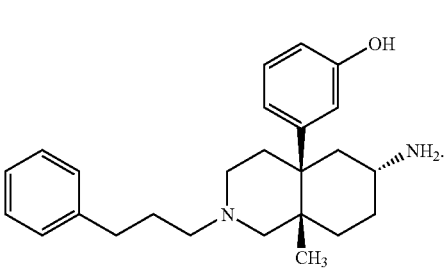

5. The compound of claim 1, which is represented by the formula:

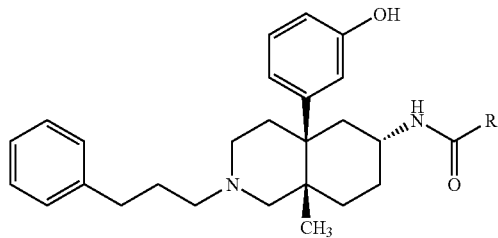

wherein R is

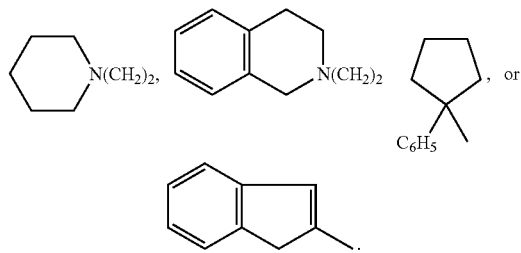

6. The compound of claim 1, wherein the substituents are cis.

7. The compound of claim 1, wherein
M is hydrogen, $C_1$-$C_4$ alkyl, or $OC_{1-8}$ alkyl;
$R_1$ is $C_{1-8}$ alkyl or $C_{1-8}$ alkylaryl;
$R_2$ is =O, hydrogen, or $NR_7R_8$;
W is hydrogen or OH; and
$R_3$ is $C_{1-3}$ alkyl.

8. The compound of claim 1, wherein W is $NH_2$.

9. The compound of claim 1, wherein W is $NHC_{1-8}$ alkyl.

10. The compound of claim 1, wherein W is $N(R_4)_2$, and each $R_4$ therein is, independently, a $C_{1-8}$ alkyl group.

11. The compound of claim 1, which is in the form of a pharmaceutically acceptable salt.

12. The compound of claim 1, wherein the compound is in the form of a salt of an acid.

13. The compound of claim 1, which is isotopically labeled.

14. The compound of claim 9, wherein the acid is hydrochloric acid, p-toluenesulfonic acid, fumaric acid, citric acid, succinic acid, salicylic acid, oxalic acid, hydrobromic acid, phosphoric acid, methanesulfonic acid, tartaric acid, maleic acid, di-p-toluoyl tartaric acid, acetic acid, sulfuric acid, hydroiodic acid, or mandelic acid.

15. A pharmaceutical composition, comprising the compound of claim 1 and a pharmaceutically acceptable carrier or diluent.

* * * * *

UNITED STATES PATENT AND TRADEMARK OFFICE
CERTIFICATE OF CORRECTION

PATENT NO.       : 7,476,679 B2
APPLICATION NO.  : 11/189068
DATED            : January 13, 2009
INVENTOR(S)      : Frank I Carroll et al.

It is certified that error appears in the above-identified patent and that said Letters Patent is hereby corrected as shown below:

Column 1, line 24, "obesity depression and other CNS disorders"
   should read -- obesity, depression and other CNS disorders --;
      line 55, "reported that trans-4a-aryldecahydroiso-"
   should read -- reported that *trans*-4a-aryldecahydroiso- --;
      line 58, "N-substituent in the trans-"
   should read -- N-substituent in the *trans*- --;
      line 61, "N-methyl"    should read -- *N*-methyl --;
      line 62, "N-(cyclopropylm-"   should read -- *N*-(cyclopropylm- --;
      line 65, "N-(cyclopropylmethyl)"    should read -- *N*-(cyclopropylmethyl) --.

Column 2, line 39, "(CH2)$_k$(Het),"    should read -- (CH$_2$)$_k$(Het), --.

Column 3, lines 10-14, " 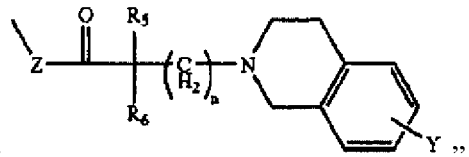 "

should read -- 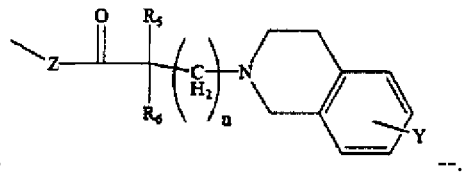 --.

Column 3, lines 15-20, " 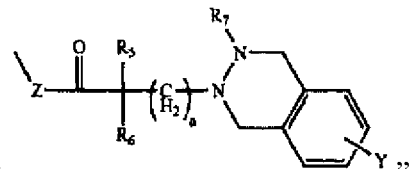 "

should read -- 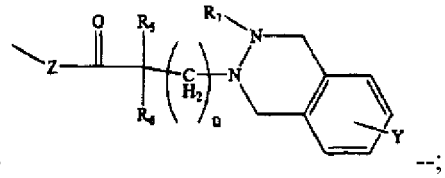 --;

UNITED STATES PATENT AND TRADEMARK OFFICE
CERTIFICATE OF CORRECTION

PATENT NO. : 7,476,679 B2  Page 2 of 6
APPLICATION NO. : 11/189068
DATED : January 13, 2009
INVENTOR(S) : Frank I Carroll et al.

It is certified that error appears in the above-identified patent and that said Letters Patent is hereby corrected as shown below:

lines 22-30, " 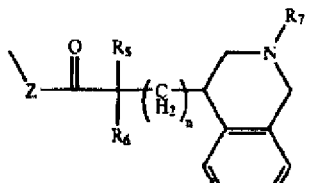 "

should read -- 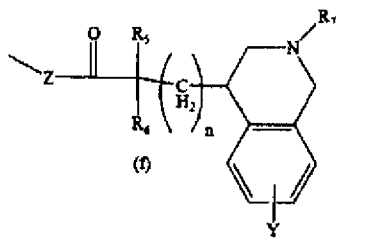 --.

Column 5, lines 18-21, " 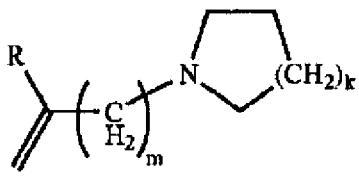 "

should read -- 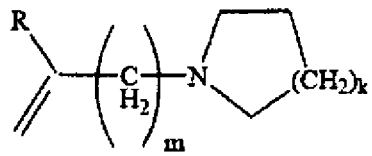 --;

lines 23-26, " 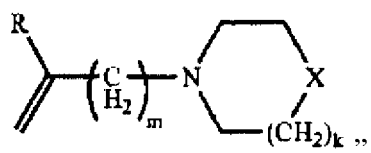 "

UNITED STATES PATENT AND TRADEMARK OFFICE
CERTIFICATE OF CORRECTION

PATENT NO. : 7,476,679 B2
APPLICATION NO. : 11/189068
DATED : January 13, 2009
INVENTOR(S) : Frank I Carroll et al.

It is certified that error appears in the above-identified patent and that said Letters Patent is hereby corrected as shown below:

should read -- 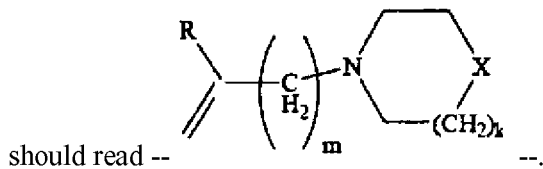 --.

Column 8, line 3, "(CH2)$_k$(Het)," should read -- (CH$_2$)$_k$(Het), --;

lines 50-57, " 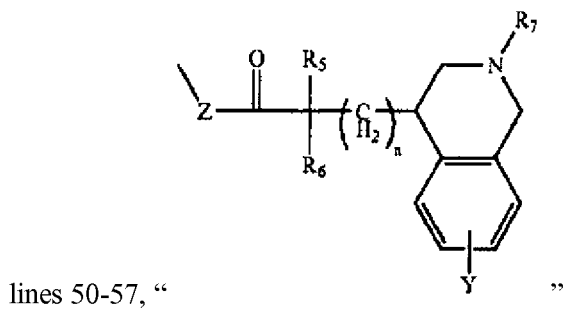 "

should read -- 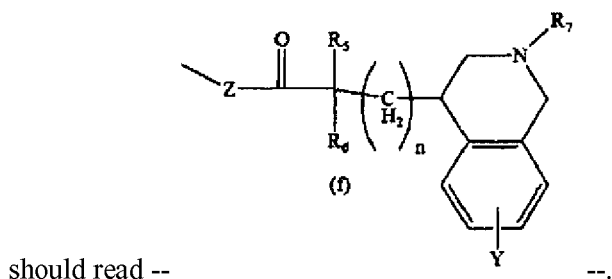 --.

Column 10, lines 45-49, " 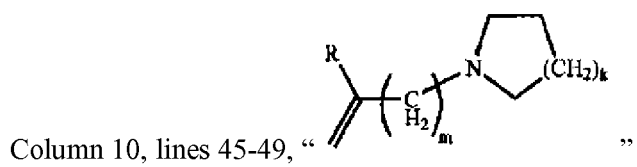 "

should read -- 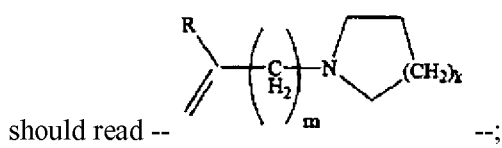 --;

UNITED STATES PATENT AND TRADEMARK OFFICE
CERTIFICATE OF CORRECTION

PATENT NO. : 7,476,679 B2
APPLICATION NO. : 11/189068
DATED : January 13, 2009
INVENTOR(S) : Frank I Carroll et al.

It is certified that error appears in the above-identified patent and that said Letters Patent is hereby corrected as shown below:

lines 51-53, " 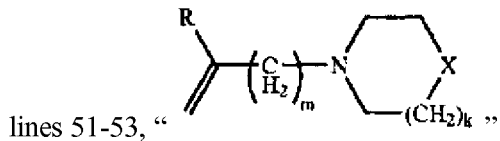 "

should read -- 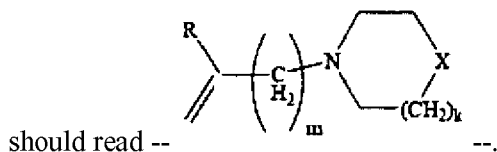 --.

Column 14, lines 40-43, " 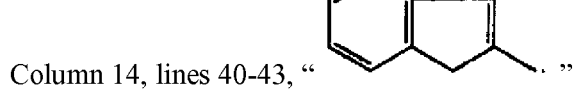 "

should read -- 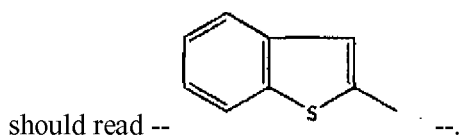 --.

Column 15, lines 28-29, "and $^{125}$I, isotopes are"
should read -- and $^{125}$I isotopes are --.

Column 18, line 19, "similar to 6a.HCl the"
should read -- similar to 6a·HCl the --.

Column 19, line 34, "($C_{17}H_{26}ClNO.0.75H_2O$)"
should read -- ($C_{17}H_{26}ClNO·0.75H_2O$) --.

Column 20, line 40, "($C_{24}H_{32}ClNO.0.5H_2O$)"
should read -- ($C_{24}H_{32}ClNO·0.5H_2O$) --;
line 60, "($C_{25}H_{34}ClNO.0.5H_2O$)"
should read -- ($C_{25}H_{34}ClNO·0.5H_2O$) --;

Column 26, line 17, "($C_{33}H_{49}Cl_2N_3O_2.2.75H_2O$)"
should read -- ($C_{33}H_{49}Cl_2N_3O_2·2.75H_2O$) --.

UNITED STATES PATENT AND TRADEMARK OFFICE
CERTIFICATE OF CORRECTION

PATENT NO. : 7,476,679 B2
APPLICATION NO. : 11/189068
DATED : January 13, 2009
INVENTOR(S) : Frank I Carroll et al.

It is certified that error appears in the above-identified patent and that said Letters Patent is hereby corrected as shown below:

Column 27, line 1, "111.1," should read -- 121.1, --;
line 9, "$(C_{37}H_{49}Cl_2N_3O_2.2H_2O)$"
should read -- $(C_{37}H_{49}Cl_2N_3O_2 \cdot 2H_2O)$ --;
line 63, "$(C_{37}H_{47}ClN_3O_2.0.75H_2O)$"
should read -- $(C_{37}H_{47}ClN_3O_2 \cdot 0.75H_2O)$ --.

Column 28, line 52, "$(C_{34}H_{39}Cl_2N_2O_2S.0.75H_2O)$"
should read -- $(C_{34}H_{39}Cl_2N_2O_2S \cdot 0.75H_2O)$ --.

Column 31, lines 37-39, " 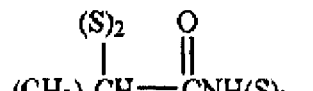 "

should read -- 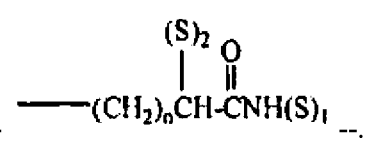 --.

Column 34, lines 17-21, " 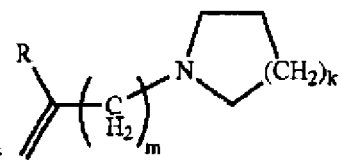 "

should read -- 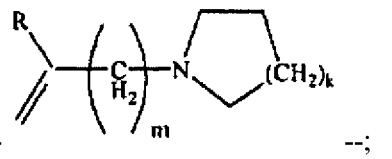 --;

lines 22-25, " 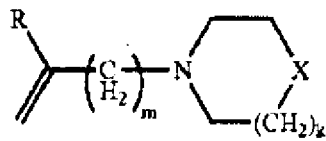 "

UNITED STATES PATENT AND TRADEMARK OFFICE
CERTIFICATE OF CORRECTION

PATENT NO. : 7,476,679 B2
APPLICATION NO. : 11/189068
DATED : January 13, 2009
INVENTOR(S) : Frank I Carroll et al.

Page 6 of 6

It is certified that error appears in the above-identified patent and that said Letters Patent is hereby corrected as shown below:

should read -- 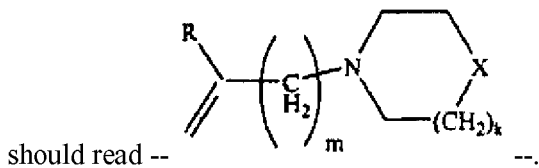 --.

Column 36, line 15, "alkylaryl," should read -- alkylaryl. --.

Column 37, lines 24-27, " 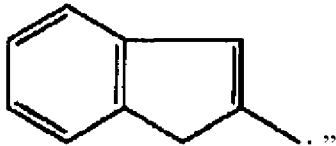 "

should read -- 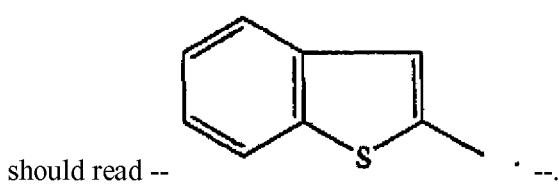 --.

Signed and Sealed this

First Day of December, 2009

David J. Kappos
*Director of the United States Patent and Trademark Office*